(12) United States Patent
Roth et al.

(10) Patent No.: US 11,684,428 B2
(45) Date of Patent: *Jun. 27, 2023

(54) ADJUSTABLE REGISTRATION FRAME

(71) Applicant: XACT ROBOTICS LTD., Caesarea (IL)

(72) Inventors: Ido Roth, Pardes Hanna (IL); Moran Shochat, Zichron Yaakov (IL); Chen Levin, Ramat Gan (IL)

(73) Assignee: XACT ROBOTICS LTD., Caesarea (IL)

(*) Notice: Subject to any disclaimer, the term of this patent is extended or adjusted under 35 U.S.C. 154(b) by 357 days.

This patent is subject to a terminal disclaimer.

(21) Appl. No.: 17/022,509

(22) Filed: Sep. 16, 2020

(65) Prior Publication Data

US 2021/0000549 A1     Jan. 7, 2021

Related U.S. Application Data

(63) Continuation of application No. 16/065,007, filed as application No. PCT/IL2016/051396 on Dec. 28, 2016, now Pat. No. 10,806,523.

(Continued)

(51) Int. Cl.
    *A61B 34/00*          (2016.01)
    *A61B 34/20*          (2016.01)
    (Continued)

(52) U.S. Cl.
    CPC .............. *A61B 34/20* (2016.02); *A61B 5/05* (2013.01); *A61B 5/064* (2013.01);
    (Continued)

(58) Field of Classification Search
    CPC ................................................... A61B 34/20
    See application file for complete search history.

(56) References Cited

U.S. PATENT DOCUMENTS 6,173,201 B1    1/2001    Front
6,282,437 B1    8/2001    Franck et al.
(Continued)

FOREIGN PATENT DOCUMENTS

DE      102008032312 A1    1/2010
JP      2002-5418885 A    12/2002
(Continued)

OTHER PUBLICATIONS

PCT International Preliminary Report on Patentability for International Application No. PCT/IL2016/051396 dated Jul. 3, 2018.

(Continued)

*Primary Examiner* — Joseph M Santos Rodriguez
(74) *Attorney, Agent, or Firm* — The Roy Gross Law Firm, LLC; Roy Gross

(57) ABSTRACT

A system for determining the position and orientation of a medical device relative to an image space during image-guided medical procedures. The system comprises a flexible pad mounted on the subject such that a part covers the region of interest. The pad incorporates detectable registration members. Prior to the procedure, the device is coupled to the pad, which is then rigidized, so that there is no movement of the registration members relative to each other and relative to the device. The fixed relationship between the device and the registration members is determined from initial images, for example using detectable markers attached to the device, enabling the pose of the device relative to the image space of images of the region of interest to be determined later, even if the device is remote from the region of interest. This minimizes exposure of the subject and medical staff to radiation.

17 Claims, 13 Drawing Sheets

Related U.S. Application Data

(60) Provisional application No. 62/387,317, filed on Dec. 28, 2015.

(51) Int. Cl.
    *A61B 5/05*          (2021.01)
    *G16H 40/63*       (2018.01)
    *G16H 50/50*       (2018.01)
    *A61B 5/06*          (2006.01)
    *A61B 90/00*       (2016.01)
    *A61B 90/50*       (2016.01)
    *A61B 17/34*       (2006.01)
    *A61B 10/02*       (2006.01)
    *A61B 90/11*       (2016.01)
    *A61B 17/00*       (2006.01)

(52) U.S. Cl.
CPC ...... *A61B 10/0233* (2013.01); *A61B 17/3403* (2013.01); *A61B 90/39* (2016.02); *A61B 90/50* (2016.02); *G16H 40/63* (2018.01); *G16H 50/50* (2018.01); *A61B 90/11* (2016.02); *A61B 2017/00566* (2013.01); *A61B 2017/3407* (2013.01); *A61B 2017/3409* (2013.01); *A61B 2034/2055* (2016.02); *A61B 2090/3954* (2016.02); *A61B 2090/3966* (2016.02); *A61B 2090/3983* (2016.02); *A61B 2090/3991* (2016.02)

(56) References Cited

U.S. PATENT DOCUMENTS

| | | |
|---|---|---|
| 6,656,143 B2 | 12/2003 | Browd |
| 6,731,966 B1 | 5/2004 | Spigelman et al. |
| 7,008,373 B2 | 3/2006 | Stoianovici et al. |
| 7,643,867 B2 | 1/2010 | Solar et al. |
| 7,911,207 B2 | 3/2011 | McFarlane et al. |
| 8,348,861 B2 | 1/2013 | Glozman et al. |
| 8,663,130 B2 | 3/2014 | Neubach et al. |
| 2004/0077972 A1 | 4/2004 | Tsonton et al. |
| 2006/0058919 A1 | 3/2006 | Sommer |
| 2006/0229641 A1 | 10/2006 | Gutpa et al. |
| 2007/0211258 A1 | 9/2007 | Lee et al. |
| 2008/0201016 A1 | 8/2008 | Finlay |
| 2008/0243142 A1 | 10/2008 | Gildenberg |
| 2010/0222684 A1 | 9/2010 | Hatzilias et al. |
| 2011/0257653 A1 | 10/2011 | Hughes et al. |
| 2012/0266898 A1 | 10/2012 | Vogele |
| 2013/0033580 A1 | 2/2013 | Fujieda et al. |
| 2014/0371584 A1 | 12/2014 | Cleary et al. |
| 2015/0126859 A1 | 5/2015 | Popovic et al. |
| 2016/0249990 A1 | 9/2016 | Glozman et al. |

FOREIGN PATENT DOCUMENTS

| | | |
|---|---|---|
| JP | 2008-544795 A | 12/2008 |
| JP | 2015-523133 A | 8/2015 |
| WO | 1999015097 A2 | 4/1999 |
| WO | 2013192598 A1 | 12/2013 |
| WO | 2015032498 A1 | 3/2015 |
| WO | 2017042823 | 3/2017 |
| WO | 2017106558 A1 | 6/2017 |

OTHER PUBLICATIONS

PCT Search Report for International Application No. PCT/IL2016/051396 dated Apr. 5, 2017.

PCT Written Opinion for International Application No. PCT/IL2016/051396 dated Apr. 5, 2017.

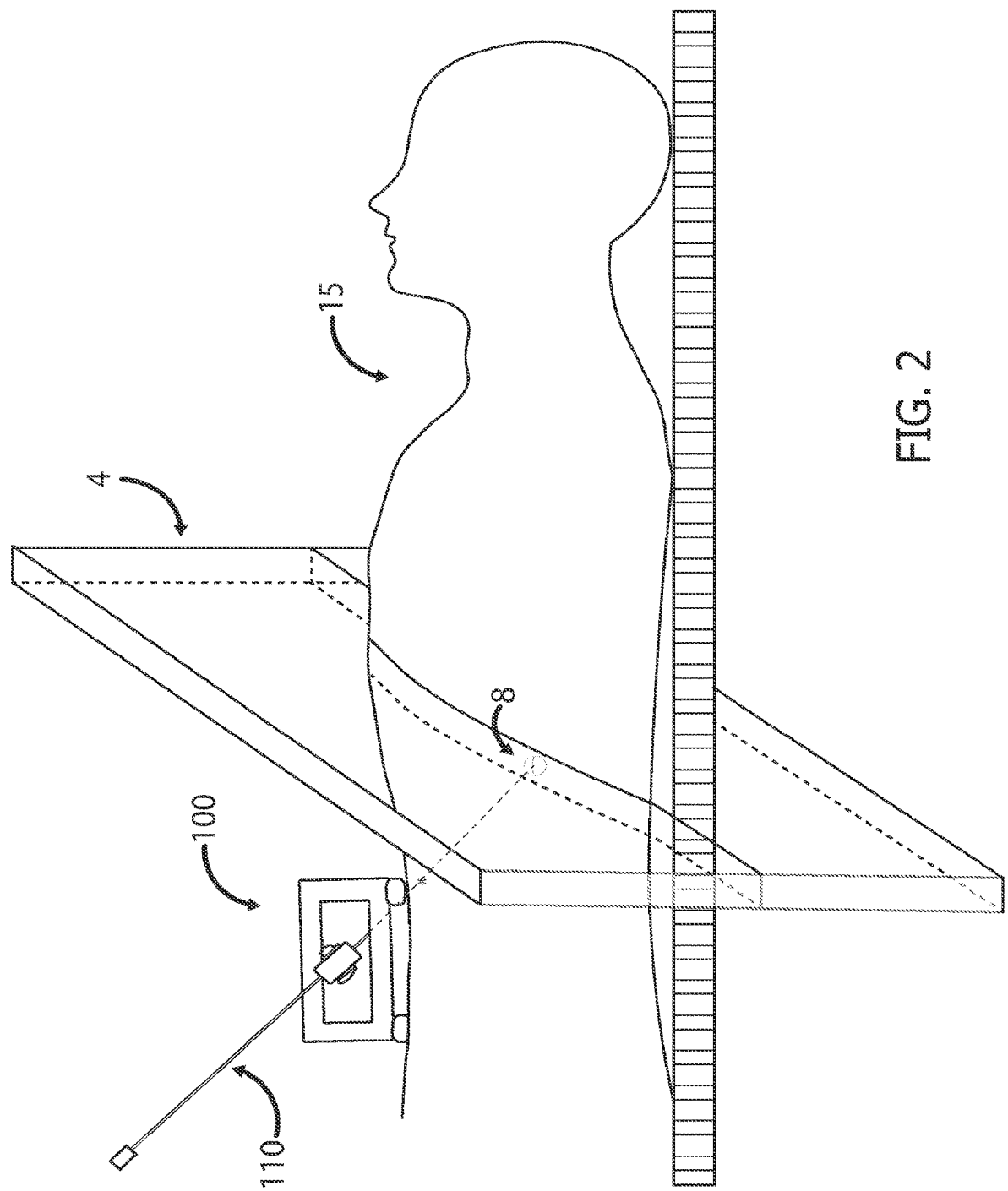

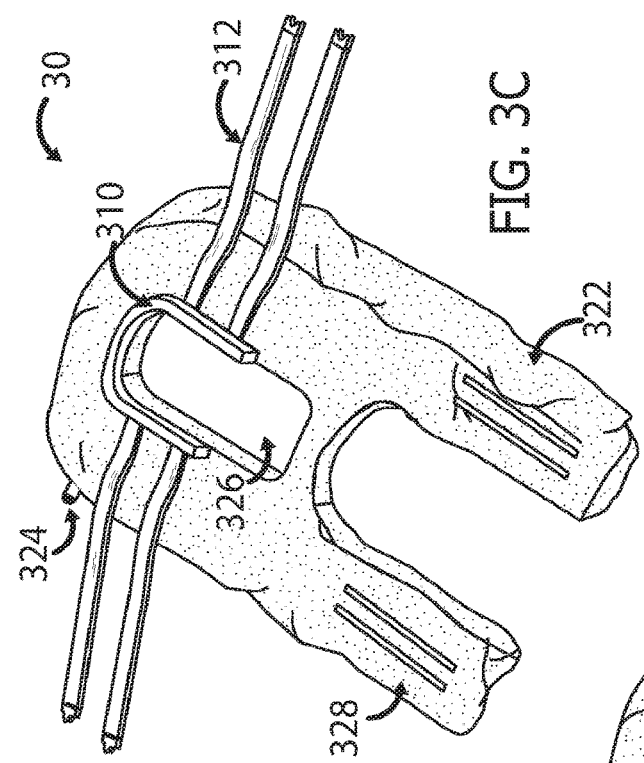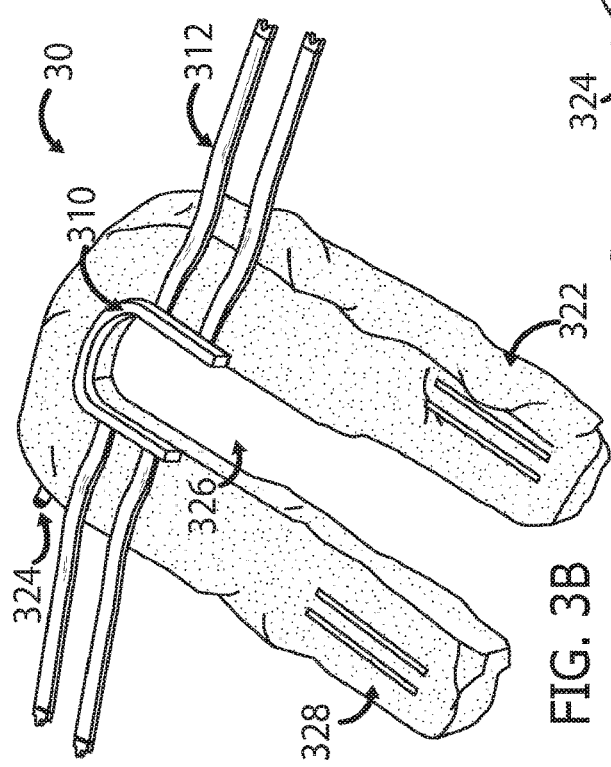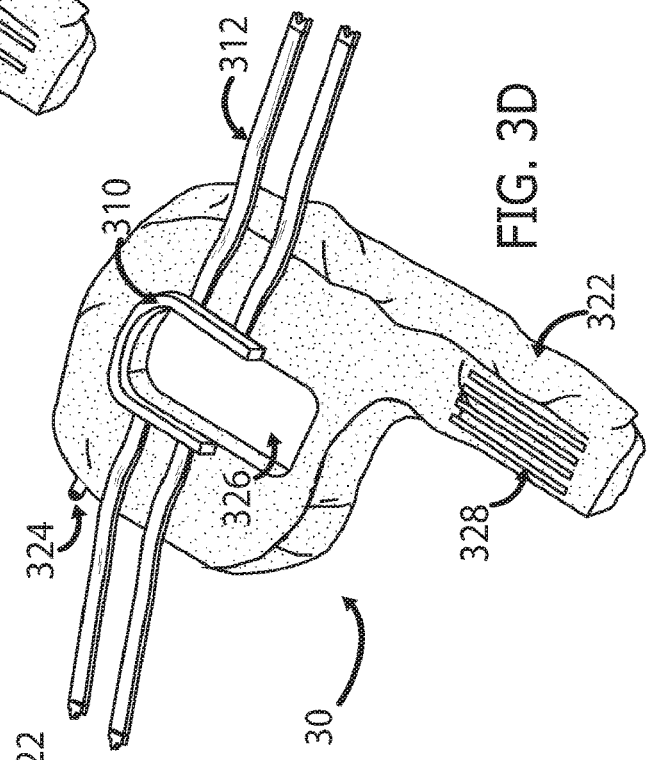

ADJUSTABLE REGISTRATION FRAME

CROSS REFERENCE TO RELATED APPLICATIONS

This application is a Continuation of U.S. Ser. No. 16/065,007 filed on Jun. 22, 2018, which is a National Phase of PCT Patent Application No. PCT/IL2016/051396 filed on Dec. 28, 2016, which claims the benefit of priority to U.S. 62/387,317 filed on Dec. 28, 2015. The contents of the above applications are all incorporated by reference as if fully set forth herein in their entirety.

FIELD OF THE INVENTION

The present disclosure relates to the field of image-guided interventional procedures, and specifically to systems and methods for determining the position and orientation of an automated medical device relative to the image space during image-guided procedures.

BACKGROUND

Many routine treatments employed in modern clinical practice involve percutaneous insertion of medical tools, such as needles and catheters, for biopsy, drug delivery and other diagnostic and therapeutic procedures. The aim of an insertion procedure is to place the tip of an appropriate medical tool safely and accurately in a target region, which could be a lesion, tumor, organ or vessel. Examples of treatments requiring insertion of such medical tools include vaccinations, blood/fluid sampling, regional anesthesia, tissue biopsy, catheter insertion, cryogenic ablation, electrolytic ablation, brachytherapy, neurosurgery, deep brain stimulation and various minimally invasive surgeries. Guidance and steering of needles in soft tissue is a complicated task that requires good three-dimensional coordination, knowledge of the patient's anatomy and a high level of experience. Therefore, image-guided automated (e.g., robotic) systems have been proposed for performing these functions. Among such systems are those described in U.S. Pat. No. 7,008,373 to Stoianovici, for "System and method for robot targeting under fluoroscopy", U.S. Pat. No. 8,348,861 to Glozman et al, for "Controlled Steering of a Flexible Needle", U.S. Pat. No. 8,663,130 to Neubach et al, for "Ultrasound Guided Robot for Flexible Needle Steering", U.S. Application Publication No. 2006/0229641 to Gupta et al, for "Guidance and Insertion System", U.S. Application Publication No. 2014/0371584 to Cleary et al, for "Patient Mounted MRI and CT Compatible Robot for Needle Guidance in Interventional Procedures", and U.S. Patent Application Publication No. 2016/0249990 to Glozman et al, for "Needle Steering by Shaft Manipulation".

When automated insertion devices are used, the exact position of the device relative to the image space must be known in order to correctly and accurately steer the medical tool, usually from a remote location, towards the target. The determination of the position of the device relative to the image space is typically done using fiducial markers, which are positioned at various locations on the device, and which are manufactured from material/s that can be detected in an image taken using an imaging system (e.g., X-Ray, CT, MRI). Detection and identification of these markers in acquired image/s is a crucial step in the process of registering the device to the image space, which allows the user to know the exact position and/or orientation of the device relative to the image space at any point throughout the procedure.

Since the registration markers are located on the device itself, in order to enable the registration process to take place, it is required that at least a portion of the device that includes marker/s thereon is included in the scans taken during the procedure. However, in some cases, due to the required insertion angle, for example, there may be a significant physical distance between the device and the region of interest of the subject. Consequently, scanning a volume sufficiently large so as to include both the region of interest and at least a portion of the device which has marker/s thereon (typically, a robotic end effector), exposes the patient and medical staff to significant amounts of radiation, when imaging modalities such as X-ray and CT are utilized in image-guided procedures.

Thus, there is a need for systems and methods that can determine the insertion device's position and orientation relative to the image space at any given moment during the insertion procedure (real-time), without necessitating inclusion of the device, or any part thereof, in the scanned volume.

The disclosures of each of the publications mentioned in this section and in other sections of the specification, are hereby incorporated by reference, each in its entirety.

SUMMARY

There are disclosed systems and methods which enable the determination of the position and orientation of an automated medical device relative to the image space at any point during an image-guided medical procedure (real-time), when the device is outside the scanned volume.

In some implementations, the automated insertion device includes a robotic arm, or a mounting base, which may be coupled to the patient's bed, for example. In other implementations, the insertion device may be body-mounted, i.e., positioned directly on the patient's body and secured thereto. In the latter case, the insertion device moves together with the patient as he/she moves (e.g., due to coughing, position adjustment, etc.).

According to some implementations, in addition to registration markers positioned on the insertion device itself, there are provided registration members positioned in/on a mounting pad, which is configured for mounting on the subject's body. The mounting pad is further configured for coupling to the insertion device. These registration members may be referred to hereinafter as "a registration frame" or "an adjustable registration frame". The mounting pad should be mounted on the subject's body such that at least a portion of the adjustable registration frame is located over or very close to the region of interest.

The adjustable registration frame may include several degrees of freedom, so that it can adjust itself together with the mounting pad as the pad adjusts to the shape of the patient's body independent of its location on the body. Following placement on the body, the mounting pad and/or the adjustable registration frame may be forced to adopt a more rigid condition in a certain spatial structure. Once the mounting pad and adjustable registration frame assume their more rigid state, the position of the adjustable registration frame relative to the insertion device, is fixed and unchangeable.

According to some implementations, the adjustable registration frame is placed within a medium that can be manipulated to prevent the frame from moving relative to the insertion device. For example, it can be placed inside a flexible mounting pad which can stiffen upon application of vacuum, cooling/heating, etc. Such a mounting pad may be filled, at least in part, with granules, which are pressed against each other upon application of vacuum, for example, thus causing the mounting pad to stiffen. It is to be understood that the term "granules" may refer to any suitable type of granules, natural or artificial, such as coffee beans, rice, sand, plastic beads, etc.

U.S. Patent Application Publication No. 2012/0266898 to Vogele, for "Immobilization Device", discloses a moldable vacuum manipulated cushion. However, the cushion is used for immobilizing the patient and it does not include an adjustable registration frame. Further, in Vogele the markers are fixed to an adapter plate attached externally to the cushion, such that they protrude away from the adapter plate. Such protruding markers may obstruct the clinician's view or actions. Further, they are at risk of being damaged or even broken. Moreover, protruding markers which are visible to the patient may appear intimidating and have a negative psychological effect on the patient.

In some implementations, the disclosed adjustable registration frame is positioned inside the mounting pad, such that it is not in the clinician's way, it is less likely to sustain damage or be broken and it is not visible to the patient. Even in implementations where the registration members are external to the mounting pad, they are small and flat enough to be unobtrusive to both the patient and the clinician.

In some implementations, the adjustable registration frame itself may be configured to stiffen or "freeze", e.g., by cooling/heating, etc. For example, it may have joints which can be locked remotely, or it may be fabricated from a material that is flexible yet can be remotely manipulated to become stiff.

In some implementations, the registration members which form together the adjustable registration frame, are configured as articulated rod assemblies, each articulated rod assembly being made up of one or more rods. In such implementations, the insertion device's position and orientation relative to the current image space (i.e., its position in terms of the coordinate system of the current image) may be determined based on the position and orientation of the rods relative to the current image space and the previously calculated (and fixed) position and orientation of the rods relative to the insertion device.

In some implementations, the registration members are configured as semi-flexible elements/strips (the terms "semi-flexible elements" and "semi-flexible strips" may be used in this disclosure interchangeably), and the insertion device's position and orientation relative to the current image space is determined based on the position and orientation of the semi-flexible strips relative to the current image space and the previously calculated (and fixed) position and orientation of the semi-flexible strips relative to the insertion device.

According to some implementations, the registration method using the disclosed adjustable registration frame is as follows:

Preparation stage: after the insertion device is coupled to the mounting pad, and the mounting pad and/or the adjustable registration frame, are caused to assume their more structurally stable states, an initial scan is obtained. The term "scan" may refer to one or more image frames taken within the scanned volume. The terms "image frame", "frame" and "slice" are used interchangeably throughout the disclosure. The initial scan includes the entire registration frame and the insertion device, so that the position and orientation (also referred to as "translation and rotation" or "transformation") of the insertion device in terms of the coordinate system ("CS") of the initial image space, as well as the position and orientation of the registration frame in terms of the coordinate system of the initial image space, can be calculated. Once the position and orientation of the insertion device and of the registration frame in terms of the coordinate system of the initial image space have been calculated, the position and orientation of the registration frame in terms of the insertion device's coordinate system, i.e., its location and orientation relative to the insertion device, can be calculated. The position and orientation of the registration frame in terms of the insertion device's coordinate system remains constant until the mounting pad and/or the adjustable registration frame is caused to return to its moldable state.

Real-time: in case a body-mounted insertion device is employed, the position and orientation of the insertion device relative to the image space may change after the initial scan is taken, due to patient movements (e.g., due to coughing, position adjustment). However, the position and orientation of the registration frame relative to the insertion device remains unchanged as long as the mounting pad and/or registration frame remain in their more structurally stable state. Thus, movement of the registration frame necessarily indicates identical movement of the insertion device. The real time scans are minimized in volume to include only the region of interest and a minimally necessary portion of the registration frame. Each real-time image includes at least a portion of the registration frame, so the transformation of the registration frame in terms of the real-time image CS can be calculated. This transformation, together with the transformation of the registration frame in terms of the insertion device CS, which is known from the initial scan, are used for determining the transformation of the insertion device in terms of the CS of each real-time image obtained throughout the insertion procedure.

The disclosed devices, systems and methods, allow to limit the scanned volume, as the scanned volume, instead of including the insertion device, which may be far from the region of interest or which due to the angle of insertion, requires a large volume to be scanned, includes only a minimal portion of the adjustable frame which can be placed over or very close to the region of interest. Thus, exposure of the patient and the medical staff to radiation is minimized.

There is thus provided in accordance with an exemplary implementation of the devices described in this disclosure, a system for determining the position and orientation of an automated medical device relative to an image space during image-guided procedures, the system comprising:
 (i) a mounting apparatus comprising:
  at least one flexible element adapted for mounting on a body of a subject and for coupling the automated medical device thereto, and
  one or more registration members positioned either on or inside the at least one flexible element,
  wherein at least one of the at least one flexible element and the one or more registration members are transformable from a moldable state to a more structurally stable state, such that upon the transformation there is substantially no relative movement between the one or more members and the automated medical device and no relative movement amongst the one or more registration members, and
 (ii) a processor configured to:
  detect at least a portion of the one or more registration members in images obtained from an imaging system, determine the position and orientation of the at least a portion of the one or more registration members relative to the image space, and determine the position and orientation of the automated medical device relative to the image space based on the determined position and orientation of the at least a portion of the one or more registration members relative to the image space and a predetermined relationship between the automated medical device and the one or more registration members.

In such a system, the at least one flexible element may comprise a granular material enclosed within a flexible covering. In such a case, the at least one flexible element may be configured to transform from the moldable state to the more structurally stable state by means of application of vacuum to the at least one flexible element. Furthermore, the one or more registration members may be coupleable to the flexible covering of the at least one flexible element.

In other implementations of such a system, the one or more registration members may comprise articulated rod assemblies, each articulated rod assembly comprising one or more rods. In such a system, the processor should be further configured to calculate the spatial angle between any two of the one or more rods. It may be further configured to calculate the minimal distance between any two of the one or more rods, or even to calculate the minimal distance points on each of the two rods, and a rod coordinate system of the two rods in the image space. In the latter case, the processor being configured to determine the position and orientation of the at least a portion of the one or more registration members relative to the image space, may comprise the processor being configured to calculate the position and orientation of at least one rod coordinate system relative to the image space.

In any of the above described systems, the one or more registration members may comprise semi-flexible elements, and the processor may then be further configured to determine, for each of the semi-flexible elements, a plane containing a pre-defined portion of the semi-flexible element in the image space. The pre-defined portion of the semi-flexible element should then be the line connecting the central points of the width of the semi-flexible element along the length of the semi-flexible element, in which case the processor may be further configured to calculate the angle between any two of the planes in the image space, or the intersection line of any two of the planes. In the latter case, the processor may be further configured to calculate, for any two of the intersection lines, the minimal distance points on at least one of the two intersection lines, and an intersection line coordinate system of the two intersection lines. If such a processor is configured to determine the position and orientation of the at least a portion of the one or more registration members relative to the image space, it may be configured to calculate the position and orientation of at least one intersection line coordinate system relative to the image space.

According to a further such implementation comprising semi-flexible elements, the one or more registration members may further include one or more threads positioned substantially horizontally to the one or more semi-flexible elements, and wherein the processor is further configured to detect at least one point of intersection between the one or more semi-flexible elements and the one or more threads. Additionally, the processor may be further configured to calculate one or more coordinate systems of the at least one intersection point. In the latter case, the processor being configured to determine the position and orientation of the at least a portion of the one or more registration members relative to the image space may comprise the processor being configured to calculate the position and orientation of the one or more coordinate systems of the at least one intersection point relative to the image space.

In yet further implementations of the above described systems, the processor is further configured to obtain the images from the imaging system.

Additional implementations can include systems such as described above, in which the mounting apparatus further comprises a base plate coupleable to the at least one flexible element, the base plate being configured to receive the automated medical device. In such a case the at least one flexible element may comprise a placement element and a registration element separate from the placement element, and wherein the placement element includes the base plate, and the registration element includes the one or more registration members.

Furthermore in any of the previously described systems, the mounting apparatus may further comprise one or more straps configured to secure the at least one flexible element to the body of the subject. Finally, the imaging system may be any one of an X-ray fluoroscopic system, a CT system, a cone beam CT system, a CT fluoroscopy system, an MRI system and an ultrasonic system.

Alternative implementations of exemplary systems according to the present disclosure may further involve a system for determining the position and orientation of an automated medical device relative to an image space during image-guided procedures, the system comprising:

(i) a mounting apparatus comprising:

at least one flexible element adapted for mounting on a body of a subject and for coupling the automated medical device thereto, and one or more registration members positioned either on or inside the at least one flexible element, and (ii) a processor configured to:

obtain one or more initial images of the mounting apparatus and the automated medical device coupled thereto, detect the one or more registration members in the one or more initial images, calculate one or more predetermined geometric parameters, to define the relationship between the one or more registration members, store the calculated values of the one or more predetermined geometric parameters, calculate the position and orientation of the one or more registration members relative to the image space of the one or more initial images, calculate the position and orientation of the automated medical device relative to the image space of the one or more initial images, determine the position and orientation of the one or more registration members relative to the automated medical device based on the calculated positions and orientations of the automated medical device and of the one or more registration members relative to the image space of the one or more initial images, obtain one or more real-time images of a region of interest, the one or more real-time images including at least two portions of at least one of the one or more registration members, detect the at least two portions of the at least one of the one or more registration members in the one or more real-time images, calculate the one or more predetermined geometric parameters in real-time, to define the relationship between the at least two portions of the at least one of the one or more registration members in the one or more real-time images, compare the real-time values of the one or more predetermined geometric parameters to the stored values of the one or more predetermined geometric parameters and identify the at least one of the one or more registration members, calculate the position and orientation of the identified at least one of the one or more registration members relative to the image space of the one or more real-time images, and determine the position and orientation of the automated medical device relative to the image space of the one or more real-time images based on the calculated position and orientation of the identified at least one of the one or more registration members relative to the image space of the one or more real-time images and the determined position and orientation of the at least one of the one or more registration members relative to the automated medical device.

In such a system, the at least one flexible element may be configured to transform from a moldable state to a more structurally stable state, and upon transformation of the at least one flexible element into its more structurally stable state, there should be substantially no movement of the one or more registration members relative to each other and relative to the automated medical device. Alternatively or additionally, the one or more registration members are configured to transform from a moldable state to a more structurally stable state, such that upon the transformation, there should be substantially no movement of the one or more registration members relative to each other and relative to the automated medical device.

In the systems described in the previous two paragraphs, the one or more registration members may comprise articulated rod assemblies, each articulated rod assembly comprising one or more rods. Alternatively, the one or more registration members may comprise semi-flexible elements. Additionally, the predetermined geometric parameters may include one or more of angles, distances, lengths, shapes, planes, relative positions and coordinate systems. Finally any of these systems may further comprise one or more registration markers attached to the automated medical device, the processor being further configured to detect the one or more registration markers.

Still other example implementations may involve a method for determining the position and orientation of an automated medical device relative to an image space during image-guided procedures, using a system comprising a processor and a mounting apparatus having at least one flexible element adapted for mounting on a body of a subject and for coupling the automated medical device thereto, and one or more registration members positioned either on or inside the at least one flexible element, wherein at least one of the at least one flexible element and the one or more registration members is transformable from a moldable state to a more structurally stable state, such that upon the transformation there is substantially no movement of the one or more registration members relative to each other and relative to the automated medical device, the method comprising:

(i) detecting at least two portions of at least one of the one or more registration members in images obtained from an imaging system, following the transformation of the at least one of the at least one flexible element and the one or more registration members from the moldable state to the more structurally stable state, (ii) determining the positions and orientations of the at least two portions of the at least one of the one or more registration members relative to the image space, and (iii) determining the position and orientation of the automated medical device relative to the image space based on the determined positions and orientations of the at least two portions of the at least one of the one or more registration members relative to the image space, and a predetermined relationship between the automated medical device and the one or more registration members.

In such a method, the one or more registration members may comprise articulated rod assemblies, each articulated rod assembly comprising one or more rods. In such a situation, the step of determining the positions and orientations of the at least two portions of the at least one of the one or more registration members relative to the image space may include:

calculating the minimal distance between at least two of the one or more rods, the minimal distance points on the at least two rods, and a rod coordinate system of the at least two rods, and calculating the position and orientation of the rod coordinate system relative to the image space.

The method may further comprise the step of calculating the spatial angles between at least two of the one or more rods. Furthermore, the one or more registration members may comprise semi-flexible elements, in which case, the step of determining the positions and orientations of the at least two portions of the at least one of the one or more registration members relative to the image space may include finding, for at least two of the semi-flexible elements, a plane containing at least a pre-defined portion of the semi-flexible element. The step of determining the positions and orientations of the at least two portions of the at least one of the one or more registration members relative to the image space may then further include finding the intersection line of any two of the planes. If this is performed, then the step of determining the positions and orientations of the at least two portions of the at least one of the one or more registration members relative to the image space further may include calculating, for any two of the intersection lines, the minimal distance between the two intersection lines, the minimal distance points on at least one of the two intersection lines, and an intersection line coordinate system of the two intersection lines. The step of determining the positions and orientations of the at least two portions of the at least one of the one or more registration members relative to the image space may then further include calculating the position and orientation of the intersection line coordinate system relative to the image space.

Any of the above described methods may further comprise the step of calculating the angle between any two of the planes.

Furthermore in any of the above described methods in which the one or more registration members comprise semi-flexible elements, the one or more registration members may further include one or more threads positioned substantially horizontally to the one or more semi-flexible elements, and wherein the step of determining the positions and orientations of the at least two portions of the at least one of the one or more registration members relative to the image space may include detecting at least one point of intersection between the one or more semi-flexible elements and the one or more threads. In such a situation, the step of determining the positions and orientations of the at least two portions of the at least one of the one or more registration members relative to the image space may further include calculating one or more coordinate systems of the at least one intersection point. The step of determining the positions and orientations of the at least two portions of the at least one of the one or more registration members relative to the image space may then further include calculating the position and orientation of the one or more coordinate systems of the at least one intersection point relative to the image space.

Finally any of the above described methods may further comprise the step of obtaining the images from the imaging system.

Yet other implementations perform a method for determining the position and orientation of an automated medical device relative to an image space, using a mounting apparatus having at least one flexible element adapted for mounting on a body of a subject and for coupling of the automated medical device thereto, and one or more registration members positioned either on or inside the at least one flexible element, and a processor, the method comprising:

- obtaining one or more initial images of the mounting apparatus and the automated medical device coupled thereto,
- detecting the one or more registration members in the one or more initial images,
- calculating one or more predetermined geometric parameters, to define the relationship between the one or more registration members,
- storing the calculated values of the one or more predetermined geometric parameters,
- calculating the position and orientation of the one or more registration members relative to the image space of the one or more initial images,
- calculating the position and orientation of the automated medical device relative to the image space of the one or more initial images,
- determining the position and orientation of the one or more registration members relative to the automated medical device based on the calculated positions and orientations of the automated medical device and of the one or more registration members relative to the image space of the one or more initial images,
- obtaining one or more real-time images of a region of interest, the one or more real-time images including at least two portions of at least one of the one or more registration members,
- detecting the at least two portions of the at least one of the one or more registration members in the one or more real-time images,
- calculating the one or more predetermined geometric parameters in real-time, to define the relationship between the at least two portions of the at least one of the one or more registration members in the one or more real-time images,
- comparing the real-time values of the one or more predetermined geometric parameters to the stored values of the one or more predetermined geometric parameters and identifying the at least one of the one or more registration members,
- determining the position and orientation of the identified at least one of the one or more registration members relative to the image space of the one or more real-time images, and
- determining the position and orientation of the automated medical device relative to the image space of the one or more real-time images based on the determined position and orientation of the identified at least one of the one or more registration members relative to the image space of the one or more real-time images and the determined position and orientation of the at least one of the one or more registration members relative to the automated medical device.

In such a method, the at least one flexible element may be configured to transform from a moldable state to a structurally more stable state, and upon transformation of the at least one flexible element into the structurally more stable state, there should be substantially no movement of the one or more registration members relative to each other and relative to the automated medical device. Alternatively or additionally, the one or more registration members may be configured to transform from a moldable state to a structurally more stable state, and upon transformation of the one or more registration members into the more structurally stable state, there should be substantially no movement of the one or more registration members relative to each other and relative to the automated medical device.

In any of the latter methods, the one or more registration members may comprise articulated rod assemblies, each articulated rod assembly comprising one or more rods, and the one or more registration members may comprise semi-flexible elements.

Finally, in these methods, the predetermined geometric parameters may include one or more of: angles, distances, lengths, shapes, planes, relative positions and coordinate systems.

According to yet further implementations of the systems of the present disclosure, there is provided a system for determining the position and orientation of an automated medical device relative to an image space during image-guided procedures, the system comprising:

(i) at least one registration marker attached to the automated medical device,
(ii) a mounting apparatus comprising:
  at least one flexible element adapted for mounting on a body of a subject and for coupling the automated medical device thereto,
  an adjustable registration frame comprised of one or more registration members positioned either on or inside at least one of the at least one flexible elements, wherein at least one of the at least one flexible element and the adjustable registration frame is transformable from a moldable state to a more structurally stable state, such that upon the transformation there is substantially no relative movement between the adjustable registration frame and the automated medical device and substantially no relative movement amongst the registration members of the adjustable registration frame, and
(iii) a processor configured to:
  obtain one or more initial images of the mounting apparatus and the automated medical device coupled thereto,
  detect the at least one registration marker and the adjustable registration frame in the one or more initial images,
  determine the position and orientation of the automated medical device relative to the image space of the one or more initial images,
  determine the position and orientation of the adjustable registration frame relative to the image space of the one or more initial images,
  determine the position and orientation of the adjustable registration frame relative to the automated medical device based on the determined positions and orientations of the automated medical device and of the adjustable registration frame relative to the image space of the one or more initial images, obtain one or more real-time images of a region of interest, the one or more real-time images including at least a portion of the adjustable registration frame, detect the at least a portion of the adjustable registration frame in the one or more real-time images, determine the position and orientation of the at least a portion of the adjustable registration frame relative to the one or more real-time images, and determine the position and orientation of the automated medical device relative to the one or more real-time images based on the determined position and orientation of the at least a portion of the adjustable registration frame relative to the one or more real-time images and the determined position and orientation of the adjustable registration frame relative to the automated medical device.

In this system, the one or more registration members may comprise articulated rod assemblies, each articulated rod assembly comprising one or more rods. Alternatively and additionally, the one or more registration members may comprise semi-flexible elements.

Still other exemplary implementations described in this disclosure involve a method for determining the position and orientation of an automated medical device relative to an image space during image-guided procedures, using a system comprising at least one registration marker attached to the automated medical device, a mounting apparatus having at least one flexible element adapted for mounting on a body of a subject and for coupling the automated medical device thereto and an adjustable registration frame positioned either on or inside the at least one flexible element, and at least one processor, the method comprising:

obtaining one or more initial images of the mounting apparatus and the automated medical device coupled thereto, detecting the at least one registration marker and the adjustable registration frame in the one or more initial images, determining the position and orientation of the automated medical device relative to the one or more initial images, determining the position and orientation of the adjustable registration frame relative to the one or more initial images, determining the position and orientation of the adjustable registration frame relative to the automated medical device based on the determined positions and orientations of the automated medical device and of the adjustable registration frame relative to the one or more initial images, obtaining one or more real-time images of a region of interest, the one or more real-time images including at least a portion of the adjustable registration frame, detecting the at least a portion of the adjustable registration frame in the one or more real-time images, determining the position and orientation of the at least a portion of the adjustable registration frame relative to the one or more real-time images, and determining the position and orientation of the automated medical device relative to the one or more real-time images based on the determined position and orientation of the at least a portion of the adjustable registration frame relative to the one or more real-time images and the determined position and orientation of the adjustable registration frame relative to the automated medical device.

In such a method, the at least one flexible element may be configured to transform from a moldable state to a structurally more stable state, and upon transformation of the at least one flexible element into the structurally more stable state, there should be substantially no relative movement between the adjustable registration frame and the automated medical device. Additionally, in this method, the adjustable registration frame may be configured to transform from a moldable state to a structurally more stable state, and upon transformation of the adjustable registration frame into the structurally stable state, there should be substantially no relative movement between the adjustable registration frame and the automated medical device.

In any of the latter methods, the adjustable registration frame may comprise one or more articulated rod assemblies, each articulated rod assembly comprising one or more rods. Alternatively or additionally, the adjustable registration frame may comprise one or more semi-flexible elements.

Implementations of the systems and methods described above may further include any of the features described in the present disclosure, including any of the features described hereinabove in relation to other system or method implementation.

It is to be understood that although the examples used throughout this disclosure relate to systems and methods for insertion of a needle into a subject's body, the systems and methods are not meant to be limited to insertion of a needle but are understood to include insertion of any tool intended to be inserted into a subject's body for diagnostic and/or therapeutic purposes, including a needle, port, introducer, catheter (e.g., ablation catheter), cannula, surgical tool, fluid delivery tool, or any other such insertable tool.

Further, it is to be understood that although the examples used throughout this disclosure relate to insertion devices and insertion procedures, the disclosed systems and methods may be implemented in any medical device and in any procedure that is image-guided and requires registration of a device to the image space.

The terms "user", "doctor", "physician", "clinician", "technician", "medical personnel" and "medical staff" are used interchangeably throughout this disclosure and they may refer to any person taking part in the performed medical procedure.

BRIEF DESCRIPTION OF THE DRAWINGS

Some exemplary implementations of the methods and systems of the present disclosure are described with reference to the accompanying drawings. In the drawings, like reference numbers indicate identical or substantially similar elements.

FIG. 2 shows schematically an automated insertion device mounted on the subject's body and located outside the scanned volume.

FIGS. 3B-3D show schematically exemplary mounting pads with an adjustable registration frame.

DETAILED DESCRIPTION

Figure 1:
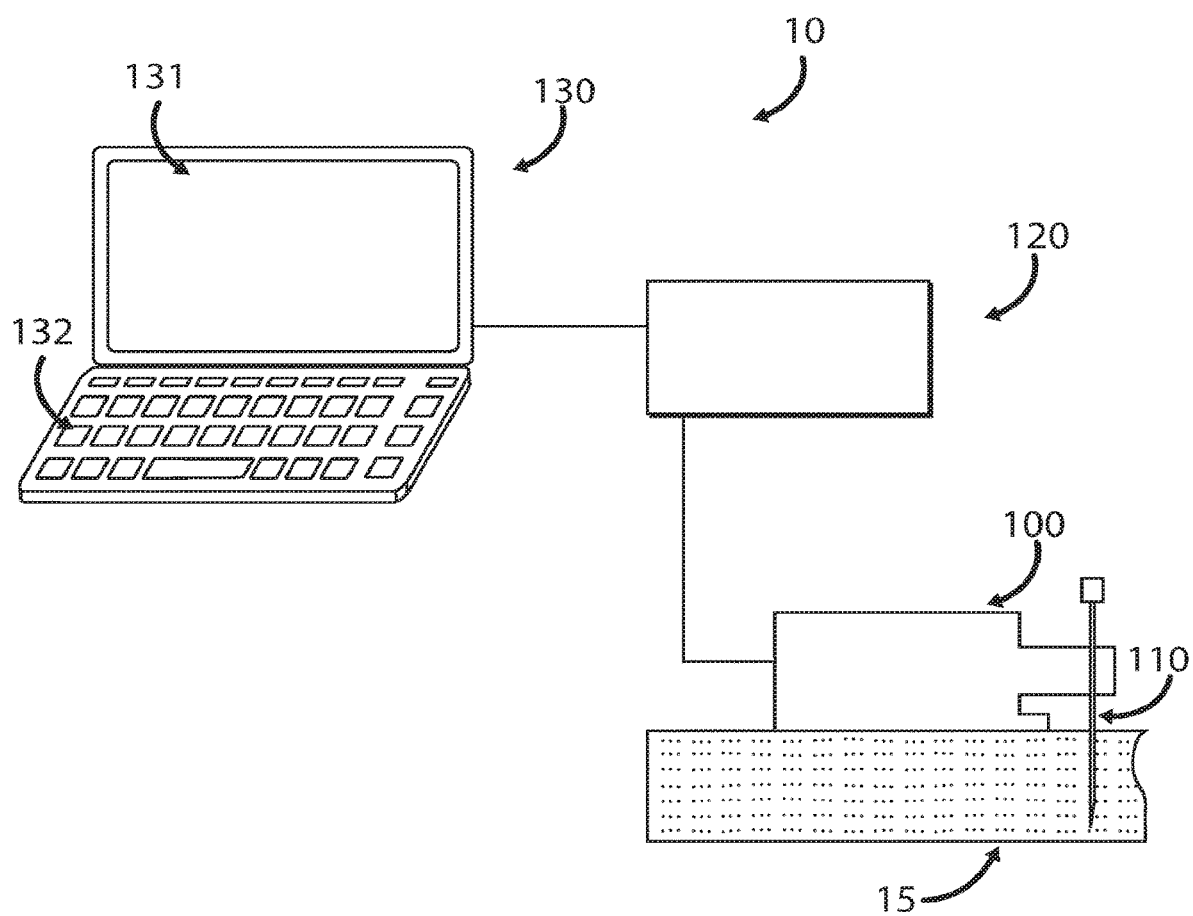
FIG. 1 shows a schematic diagram of an exemplary system for inserting a medical tool into the body of a subject.

FIG. 1 shows a schematic diagram of a system 10 for inserting a medical tool (e.g., needle) 110 into the body of a subject. The system includes an automated insertion device 100, which may be additionally configured for steering the needle during its insertion into the subject's body 15. The needle 110 may be removably coupled to the insertion device 100, such that the insertion device 100 can be used repeatedly with new needles.

In some implementations, the system 10 may include an imaging system, or it may be configured to operate in conjunction with an imaging system, such that the insertion procedure is image-guided. The utilized imaging modality may be any one of X-ray fluoroscopy, CT, cone beam CT, CT fluoroscopy, MRI, ultrasound, or any other suitable imaging modality.

The insertion device 100 may be configured to be mounted directly on the subject's body 15, as shown in FIG. 1, or it may be configured to be coupled to a dedicated arm or base secured to the patient's bed, to a cart positioned adjacent the patient's bed or to the imaging device, as described, for example, in abovementioned U.S. Patent Application Publication No. 2016/0249990.

The system 10 further comprises a computer 130, including at least one processor (not shown) for image processing, calculation of the optimal needle insertion path, etc., and a display 131. The computer 130 may be a personal computer (PC), a laptop, a tablet, a smartphone or any other processor-based device. The computer 130 may also include a user interface 132, which may be in the form of buttons, switches, keys, keyboard, computer mouse, joystick, touch-sensitive screen, etc. The display 131 and user interface 132 may be two separate components, or they may form together a single component, in case a touch-sensitive screen ("touch screen"), for example, is utilized.

The computer 130 may be configured, inter alia, to receive, process and visualize on the display 131 images from the imaging system, to calculate the optimal pathway for the needle 110 based on input from the user, i.e., entry point, target and areas to avoid en route, and to control needle steering in a closed-loop manner, i.e., generate motion commands to the insertion device 100 and receive feedback regarding the actual location of the needle 110, which is then used for real-time pathway corrections. The optimal pathway may be calculated in a two-dimensional plane or in a three-dimensional space.

The system 10 further includes a controller 120 (e.g., robot controller) for controlling the movement of the insertion device 100 and steering of the needle 110 towards the target (e.g., lesion or tumor) within the subject's body 15. The controller 120 may be a separate component, as shown in FIG. 1. Alternatively, at least a portion of the controller 120 may be embedded within the insertion device 100, and/or within the computer 130.

FIG. 2 shows schematically an automated insertion device 100 mounted on the subject's body 15. In some implementations, prior to mounting the insertion device on the subject's body, the user marks on an initial scan of the region of interest (the term "scan" may refer throughout this disclosure to one or more frames) an initial point of entry, the target and any possible obstacles en route from the entry point to the target. Then, the system software may calculate an optimal needle trajectory, which may be, for example, the trajectory which provides minimal lateral pressure on the patient's tissues. In some implementations, calculation of the optimal trajectory may include determination of the entry angle of the needle at the entry point. In other implementations, the user must input the entry angle prior to trajectory calculation. Methods for planning an insertion trajectory are disclosed, for example, in co-owned International Patent Application No. PCT/IL2015/050230 to Shochat, for "Dynamic Planning Method for Needle Insertion", which is hereby incorporated by reference in its entirety.

During the needle insertion procedure, several scans may be required in order to verify the needle's actual position, and adjust the trajectory accordingly, if needed. In order to minimize the exposure of the patient and medical staff to radiation, the scanned volume 4 is typically chosen to be as small as possible. Thus, in some cases, for example when the optimal trajectory for reaching the target 8 requires a moderate/large insertion angle relative to the axial frames of the CT system (i.e., frames generated in the axial plane, perpendicular to the long axis of the patient's body), such as larger than 25-30 degrees, the insertion device 100 may be located entirely outside the scanned volume 4, as shown in FIG. 2. Typically, registration markers are coupled to one or more of the insertion device's components, thus in case the device is located outside the scanned volume, it is not possible, using prior art methods, to register the device's 100 location relative to the image space, which is necessary in order to provide the insertion device 100 with accurate movement/steering instructions during the needle insertion procedure.

Figure 3A:
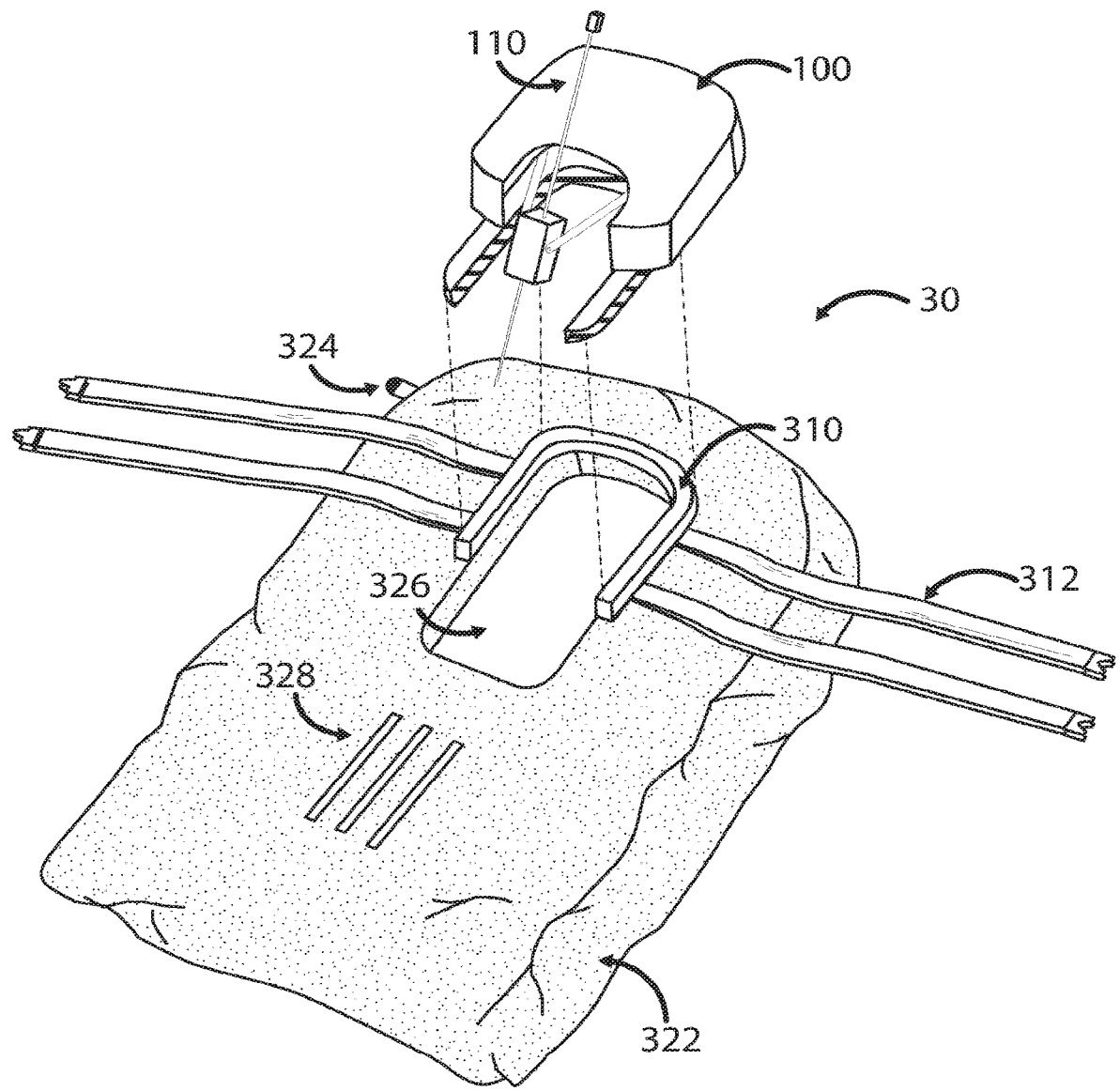
FIG. 3A shows schematically a mounting pad with an adjustable registration frame, and an insertion device, prior to coupling of the insertion device to the mounting pad.

FIG. 3A shows schematically an insertion device 100 and a mounting pad 30 prior to coupling. The insertion device 100 may be removably coupled to the mounting pad 30, such that the insertion device 100 and the mounting pad 30 are two separate units, and the insertion device 100 can be coupled to and then removed from the mounting pad 30. Alternatively, the insertion device 100 and the mounting pad 30 may be rigidly coupled to each other or they may further be configured as a single unit. The mounting pad 30 may include a base plate 310, to which the insertion device 100 is connected, in case of a body-mounted device, and it may further include one or more straps or belts 312, which secure the mounting pad 30, and thus the insertion device 100, to the subject's body. The base plate 310 and the one or more straps 312 may be an integral part of the mounting pad 30, or they may be separate components removably coupled to the mounting pad 30. Further, the one or more straps 312 may be coupled, either rigidly or removably, either to the mounting pad 30 or to the base plate 310. The base plate 310 may be "U" shaped, as shown in FIG. 3A, or it may comprise any other suitable shape, depending on the design of the insertion device 100 and/or the mounting pad 30.

According to some implementations, the mounting pad 30 may be configured as a flexible sac/cushion filled, at least in part, with granules 322, either natural or artificial, such as coffee beans, rice, sand, plastic beads, etc. The mounting pad 30 may further include a vacuum valve 324, such that when vacuum is applied to the mounting pad 30 via the valve 324, the granules 322 are pressed against each other and the mounting pad 30 stiffens. After vacuum is applied, the shape of the mounting pad 30 cannot be altered until the vacuum is cancelled and air is allowed back into the pad. It is to be understood that the use of vacuum in order to stiffen the mounting pad is merely an example, and the mounting pad may be caused to stiffen using any other suitable method, such as heating or cooling.

The mounting pad 30 further includes one or more registration members 328 (e.g., fiducial markers), which form together an adjustable registration frame for determining the insertion device's 100 position/movement, as will be explained in detail below.

In some implementations, the registration members 328 may be provided inside the mounting pad 30, together with the granules 322, such that when the pad is in its flexible/moldable form, for example, prior to application of vacuum, the registration members 328 can move around inside the mounting pad 30, or inside a limited portion of the mounting pad 30. In other implementations, the registration members 328 may be coupled to the mounting pad's cover, either as an integral part of the cover or removably coupled thereto, and either to the cover's external surface, such that the registration members 328 face the external environment, or to its internal surface, such that the registration members 328 face the granules 322 within the pad 30. In case the registration members 328 are coupled to the mounting pad's cover, then when the pad is in its flexible form, the registration members 328 can only move together with the cover. Once vacuum is applied to the mounting pad 30, and the mounting pad 30 transforms into its more solidified/rigid form, the registration members 328 can no longer move, not relative to one another, not relative to the mounting pad's cover and granules and not relative to the insertion device 100. Further, once vacuum is applied, the bottom portion of the pad 30 may conform to the shape and contours of the subject's body 15, thus providing stability to the insertion device 100 and minimizing discomfort to the subject. In some implementations, once vacuum is applied, the combination of fastened straps 312 and the mounting pad receiving the shape of the subject's body may prevent the entire mounting pad 30, and the insertion device coupled thereto, from moving relative to the subject's body during the insertion procedure. In some implementations, the mounting pad 30 may be configured such that only a portion of the pad 30 conforms to the shape of the subject's body 15 upon application of vacuum. For example, only the portion which includes the base plate 310 may conform to the shape of the subject's body 15, whereas the portion which includes the registration members 328 may remain slightly hovered above the subject's body, e.g., by having a rigid bottom portion that is configured to remain slightly elevated from the surface to which the mounting pad 30 is attached, such that movements due to breathing, for example, will not result in movement of that portion of the mounting pad 30. This may be of utmost importance in case the area of the body on which the base plate portion of the pad is positioned is not affected by breathing (i.e., does not move), for example, but the area of the body on which the portion of the pad which includes the registration members is positioned is affected by breathing, and thus detected movement of the markers might wrongfully be determined as corresponding movement of the insertion device 100, when in fact there is no movement of insertion device 100.

The registration members 328 are manufactured, at least in part, from material/s that can be detected in an image taken using an imaging system (e.g., X-Ray, CT, MRI), and are clearly distinguished from all other mounting pad elements, such as the cover and the granules. Further, the registration members' material/s should be chosen such that they will not cause imaging artifacts. In case a CT system is utilized, for example, such materials may be carbon, aluminum, polyether ether ketone (PEEK), etc. It is to be understood that the registration members 328 are provided in addition to markers positioned on the insertion device 100 itself (not shown).

The mounting pad 30 may be provided in a variety of shapes and sizes. It may be symmetrical, such as having a U-like shape, as shown in FIGS. 3B and 3C, or it may be asymmetrical, such as having a sleeve-like portion extending outwardly from one side of the pad, as shown in FIG. 3D. The mounting pad 30 may be configured as a cushion or pillow which is attached to the subject's body using the one or more straps 312, or any other suitable attachment means, or it may be configured to be worn by the subject and be configured as a designated shirt, vest, harness, etc. To allow the needle 110 access to the patient's body, the mounting pad 30 may include an opening 326, as shown in FIGS. 3A, 3C and 3D, or it may be configured to be "open ended", as shown, for example, in FIG. 3B. In some implementations, the mounting pad 30 may include two (or more) separate pads—a placement pad and a registration pad (not shown)—which may be removably coupled to each other. In such cases, the registration pad includes the registration members 328 and it is used for determining the insertion device's 100 position and orientation, and the placement pad may be used to enable stable placement of the insertion device 100 on the subject's body, for example when the insertion device is intended for placement on curved areas of the body and/or on areas that allow only limited contact area between the insertion device 100 and the body. The placement pad may further be used to provide padding under the insertion device 100 so as to minimize any discomfort or pain to the subject due to placement of the insertion device 100 directly on his/her body. The placement pad may include the base plate 310 if a base plate is employed. When used without the registration pad, the placement pad may be left in its flexible state, and it is not necessary to transform it to its rigid state, since in such a case the placement pad is not used for registration. It is to be understood that, when separate, use of the placement pad is optional, and the physician may choose not to use the placement pad and to place the insertion device, or the base plate, directly on the subject's body. In such a case the registration pad may be connectable to the base plate 310 or directly to the insertion device 100. Further, when separate, use of the registration pad may also be optional, i.e., in case that according to the optimal trajectory, the positions of the insertion device, the entry point and the target are such that at least a portion of the insertion device is necessarily within the scanned area in any required scan, there may be no need for the registration pad. When the two pads are used together, they are coupled to each other such that once vacuum is applied there is no relative movement between the two pads, and they de facto form together a single pad.

Reference is now made to FIGS. 4A-8, which illustrate an exemplary implementation of the system and method of the present disclosure. In this implementation, the registration members of the mounting pad 40 are configured as articulated rod assemblies 428, each articulated rod assembly being made up of one or more rods 430, which may be connected by joints 432, and the insertion device's position and orientation relative to the current image space, i.e., its position and orientation in terms of the coordinate system of the current image, is determined based on calculating the transformation (i.e., position and orientation) of the rods relative to the current image space and the previously calculated (and fixed) transformation of the rods relative to the insertion device, as will be explained in detail hereinbelow.

Figure 4A:
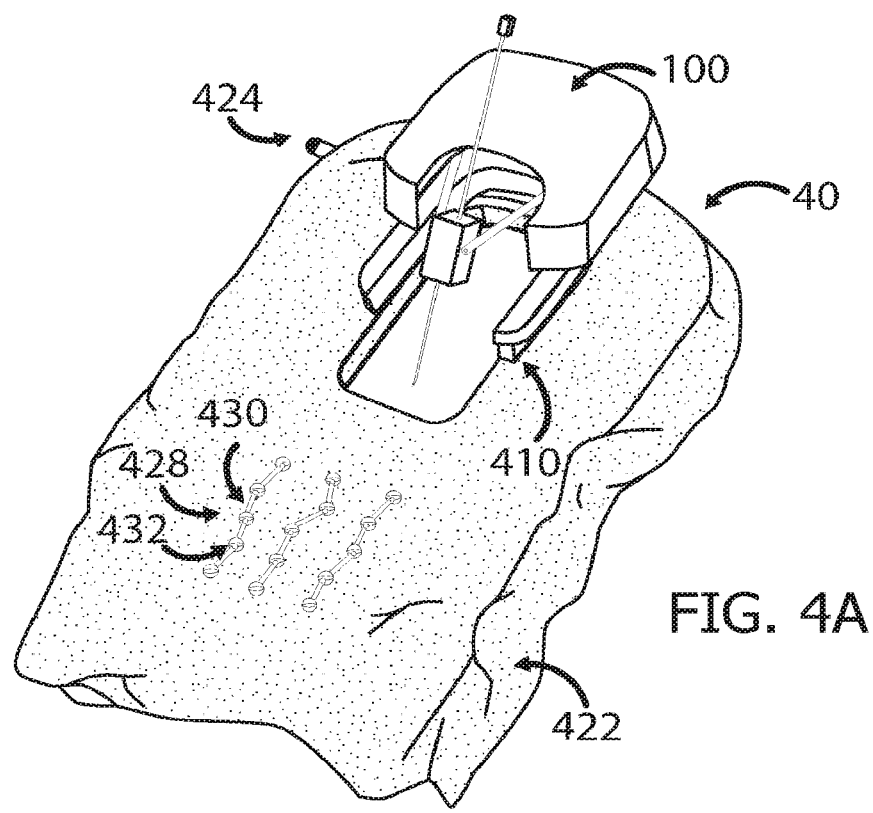
FIG. 4A shows a perspective view of an exemplary mounting pad with an adjustable registration frame, and an insertion device coupled thereto, prior to application of vacuum to the mounting pad.

FIG. 4A shows a perspective view of an exemplary mounting pad 40 configured as a flexible sac/cushion filled with granules 422, and an insertion device 100 coupled thereto, prior to application of vacuum on the mounting pad 40. It is to be understood that, although not shown, application of vacuum is carried out only after the mounting pad 40 has been secured to the subject's body, such as by using straps or belts (not shown in FIG. 4A). The insertion device 100 may be coupled to the mounting pad 40 either before or after placement of the mounting pad 40 on the subject's body.

In the implementation shown in FIG. 4A, the registration frame is comprised of three articulated rod assemblies 428, each articulated rod assembly having four rods 430 and five joints 432. It is to be understood that the registration frame is not limited to the above number of articulated rod assemblies, rods and/or joints, and it may be comprised of any number of articulated rod assemblies having any number of rods with any number of joints, as long as unique identification of rods sets, which is required for the registration procedure (see below), is enabled. The joints 432 should preferably allow each rod at least three Degrees of Freedom (DOF)—up/down, left/right and rotation. The joints 432 may be configured, for example, as spherical joints. Prior to application of vacuum to the mounting pad 40 via the valve 424, the rods 430 are free to move relative to each other, such that movement of the mounting pad 40 can result in many different spatial arrangements of the articulated rod assemblies 428 within the pad.

Figure 4B:
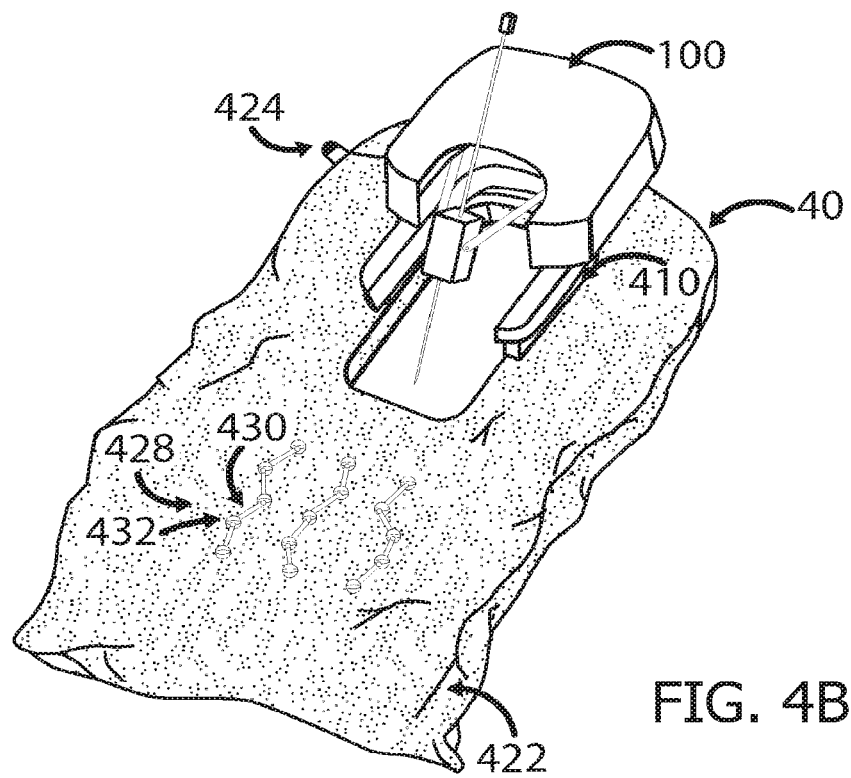
FIG. 4B shows a perspective view of the exemplary mounting pad with the exemplary adjustable registration frame and insertion device of FIG. 4A, after application of vacuum to the mounting pad.

Once vacuum is applied to the mounting pad 40, as shown in FIG. 4B, the granules 422 are pressed against each other and against the articulated rod assemblies 428, such that each articulated rod assembly 428 becomes fixated in one configuration and there is no longer any movement of the articulated rod assemblies 428 relative to each other and/or of the rods 430 of each articulated rod assembly 428 relative to the other rods of the same assembly 428. Further, once vacuum is applied, there is also no movement of the articulated rod assemblies 428 relative to the insertion device 100. Thus, the registration frame and the insertion device 100 can be regarded as one solid body, such that movement of the registration frame necessarily indicates identical movement of the insertion device. Accordingly, the position and orientation of the insertion device relative to the image space can be calculated at any point during the insertion procedure, even if the insertion device is positioned outside the scanned volume, based on the calculated position and orientation of the registration frame (or a portion thereof) relative to the image space, as described in detail hereinbelow.

Although not shown in FIG. 4B, it can be appreciated that when vacuum is applied to the mounting pad 40, the bottom portion of the pad 40 may conform, entirely or partially, to the shape of the subject's body.

After the mounting pad 40 has been secured to the subject's body, the insertion device 100 has been coupled to the mounting pad 40, and vacuum has been applied to the mounting pad 40, the clinician can initiate the initial stage of the registration procedure, also referred to as "the preparation stage".

Figure 5:
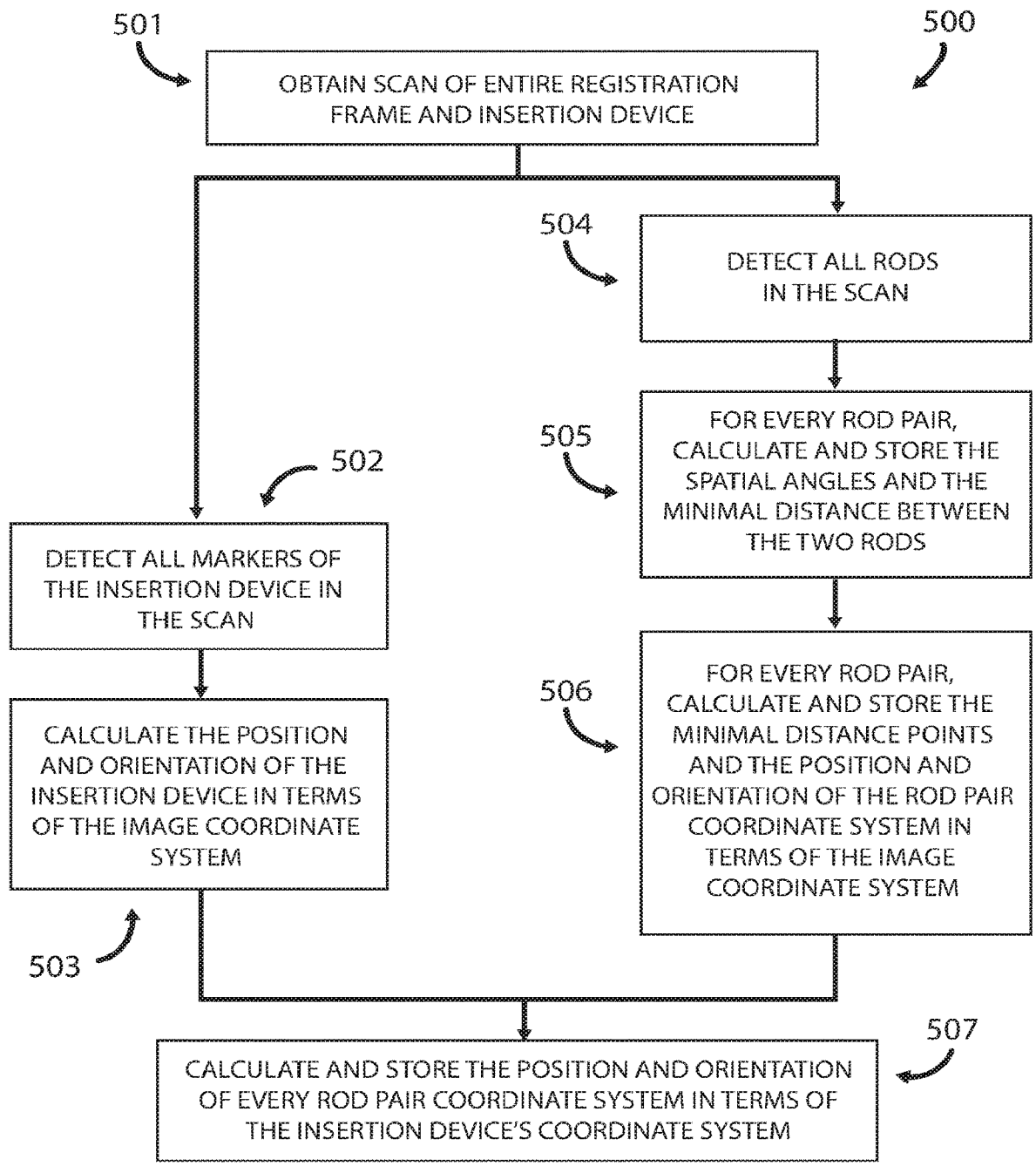
FIG. 5 shows a flowchart of the steps executed in an exemplary initial stage of a registration procedure using the adjustable registration frame of FIG. 4B.

FIG. 5 shows a flowchart 500 of the steps executed in an exemplary initial/preparation stage of a registration procedure using articulated rod assemblies.

In step 501, an initial scan of the entire registration frame and the insertion device is obtained. The initial scan includes the entire registration frame (all the articulated rod assemblies together constitute the registration frame) and the insertion device. The number of images taken during the initial scan and the spacing between the images may be determined by the user, or they may be dictated by the system software. The images may be retrieved from the imaging system in any applicable method, such as directly (i.e., an embedded system), using a communication module (e.g., transferring DICOM file(s) over a local area network) or using an external storage unit, such as a CD, DVD, USB portable drive, etc. In some implementations, the scanning may be initiated manually by the user. In other implementations, the scanning may be initiated automatically by the insertion system's software.

In step 502, the fiducial markers of the insertion device are detected using image processing techniques. These markers, which are attached to the insertion device, have known parameters, such as size and shape.

In step 503, the position and orientation of the insertion device in terms of the coordinate system of the initial image space are calculated.

In step 504, all the rods are detected in the initial scan using image processing techniques. As previously noted, the rods, which constitute the registration frame, are manufactured, at least in part, from material/s that can be identified in an image taken by an imaging system (e.g., X-Ray, CT, MRI).

In step 505, the minimal distances and spatial angles between every two rods of the registration frame are calculated and stored. This data defines each rod pair. In some implementations, the above calculations are carried out for each and every two rod combination in the registration frame. In other implementations, the above calculations are not carried out for rod pairs which are deemed impossible or very unlikely to appear in the same scan, after a filtering/ screening process is executed. Such pairs may be, for example, pairs of two rods which belong to the same articulated rod assembly but are not adjacent (i.e., rods that are not connected by a joint).

The minimal distance in three-dimensional space between two rods, if the two rods are not parallel and neither they nor their extended lines intersect each other, is the length of the segment which is uniquely simultaneously perpendicular to both rods. If two rods, or their extended lines, intersect then the minimal distance between them is zero. The spatial angles between every two rods are random and distinct. Thus, if the minimal distance and spatial angle are known, any rod pair can later be traced.

In step 506, for every two rods for which the minimal distance and spatial angle were calculated and stored in step 505, the minimal distance points (hereinafter also referred to as "MDPs") are calculated and stored. The MDPs are the unique points on the two rods at which the two rods are closest to each other, i.e., these are the two points which are joined by the segment which is uniquely simultaneously perpendicular to both rods, if the two rods are not parallel and do not intersect each other, and the length of which is the minimal distance between the two rods. The MDPs may be on the rods themselves, or they may be on the extended infinite lines of the rods (i.e., outside the range of the rods), which are restricted subsets of those lines. If two rods, or their extended infinite lines, intersect, then their MDPs are conjoined.

Each rod may have multiple MDPs, depending on the number of other rods with which it is paired. For example, if the registration frame is composed of three articulated rod assemblies each having five rods, such that the registration frame is made up of fifteen rods altogether, then each rod may have fourteen MDPs, since it may be paired up with each of the other fourteen rods, including the four rods which belong to its articulated rod assembly.

Figure 6:
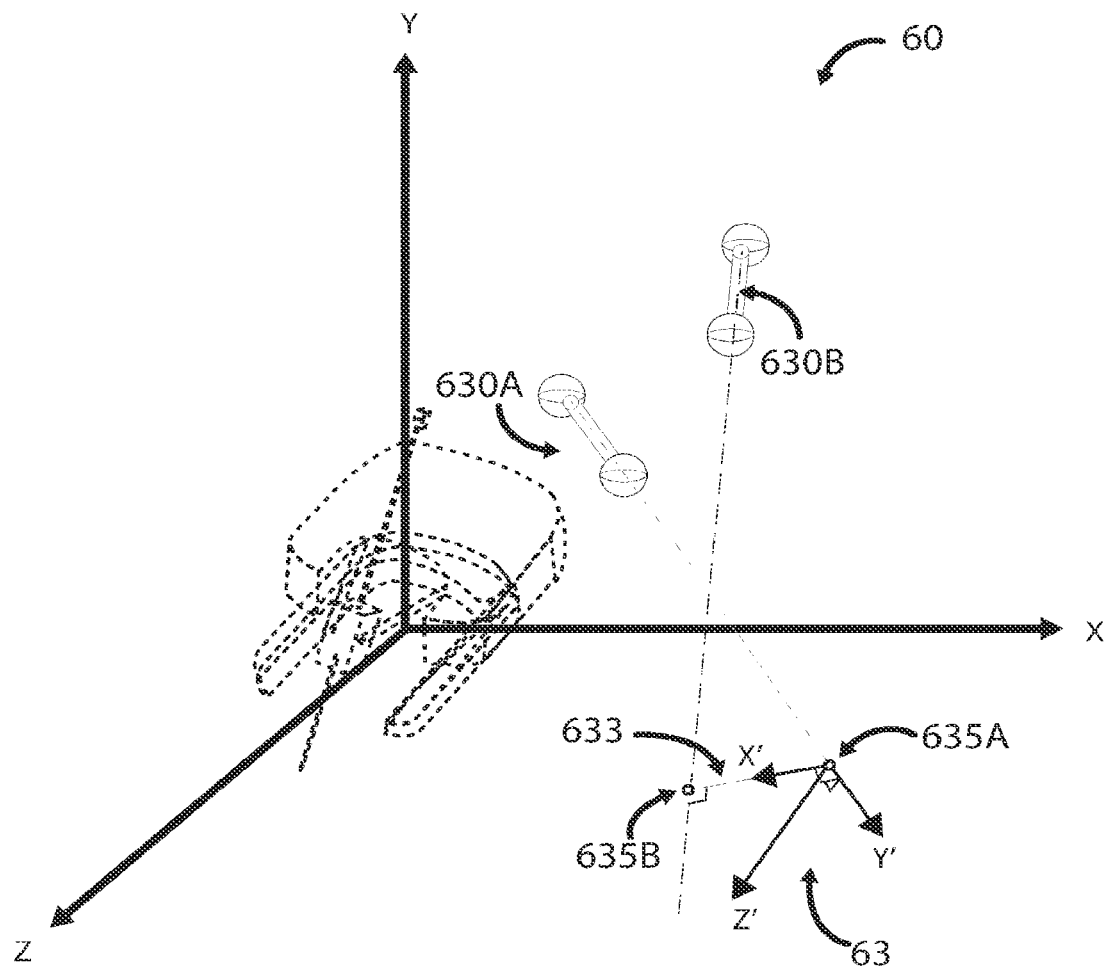
FIG. 6 shows an insertion device coordinate system and two exemplary rods, the minimal distance between the rods, the minimal distance points and the rod pair's coordinate system.

Also calculated and stored in step 506 for each rod pair is the rod pair coordinate system (hereinafter also referred to as "RPCS") in terms of the coordinate system of the initial image space, i.e., the position and orientation of the RPCS relative to the image space coordinate system. The origin of the RPCS is at the rod's MDP, and its XYZ vectors are defined by the rod or its extended line, the vector to the coupled rod's MDP, and the cross product of the first two vectors, as shown in FIG. 6.

In some implementations, if the registration frame comprises n rods, theoretically each rod may be paired up with each of the remaining n−1 rods, such that for each rod n−1 MDPs and RPCSs are found and stored. For example, if the registration frame is composed of three articulated rod assemblies each having five rods, then each rod may have fourteen MDPs and fourteen RPCSs. In other implementations, there may be certain limitations to the pairing resulting in less than n−1 MDPs and RPCSs calculated for each rod. For example, a filtering process may be executed such that each rod may be paired up with all other rods in the reference frame excluding, for example, the rods which are part of the same articulated rod assembly as that specific rod. Further, in some implementations only one RPCS is calculated for each rod pair, as demonstrated in FIG. 6.

In step 507, after having calculated the positions and orientations of the insertion device and of the RPCSs in terms of the coordinate system of the initial image space, in steps 503 and 506 respectively, the positions and orientations of the RPCSs in terms of the coordinate system of the insertion device are calculated, based on the above two calculations.

Since there is no relative movement between the registration frame and the insertion device after vacuum is applied to the mounting pad, the positions and orientations of the RPCSs in terms of the coordinate system of the insertion device will remain unchanged until the vacuum is cancelled. This enables the insertion device to be positioned outside the scanned volume, as the position and orientation of the insertion device in terms of the coordinate systems of each of the images obtained throughout the insertion procedure can be calculated based on the known positions and orientations of the RPCSs in terms of the coordinate system of the insertion device, and the calculation of the positions and orientations of the RPCSs that are included in the scanned volume in terms of the coordinate system of a specific new image, as described in detail in FIG. 8 below.

FIG. 6 shows the insertion device's coordinate system 60, and two exemplary rods 630A and 630B. Also shown is the minimal distance 633 between the two rods, i.e., the length of the segment which is perpendicular to both rods, or to their extended lines, as shown in FIG. 6. Further shown are the rods' MDPs 635A and 635B in relation to each other, and the rod pair coordinate system 63 of the rod pair 630A, 630B. The origin of the RPCS 63 is located, in this example, at the MDP 635A of rod 630A, since the rod pair in question is (630A, 630B). The origin of the RPCS of rod pair (630B, 630A) would have been located at the MDP 635B of rod 630B. The X'Y'Z' vectors of the RPCS 63 are defined by the rod 630A (or its extended infinite line), the vector to the MDP 635B of the coupled rod 630B, and the cross product of the first two vectors.

Figure 7A:
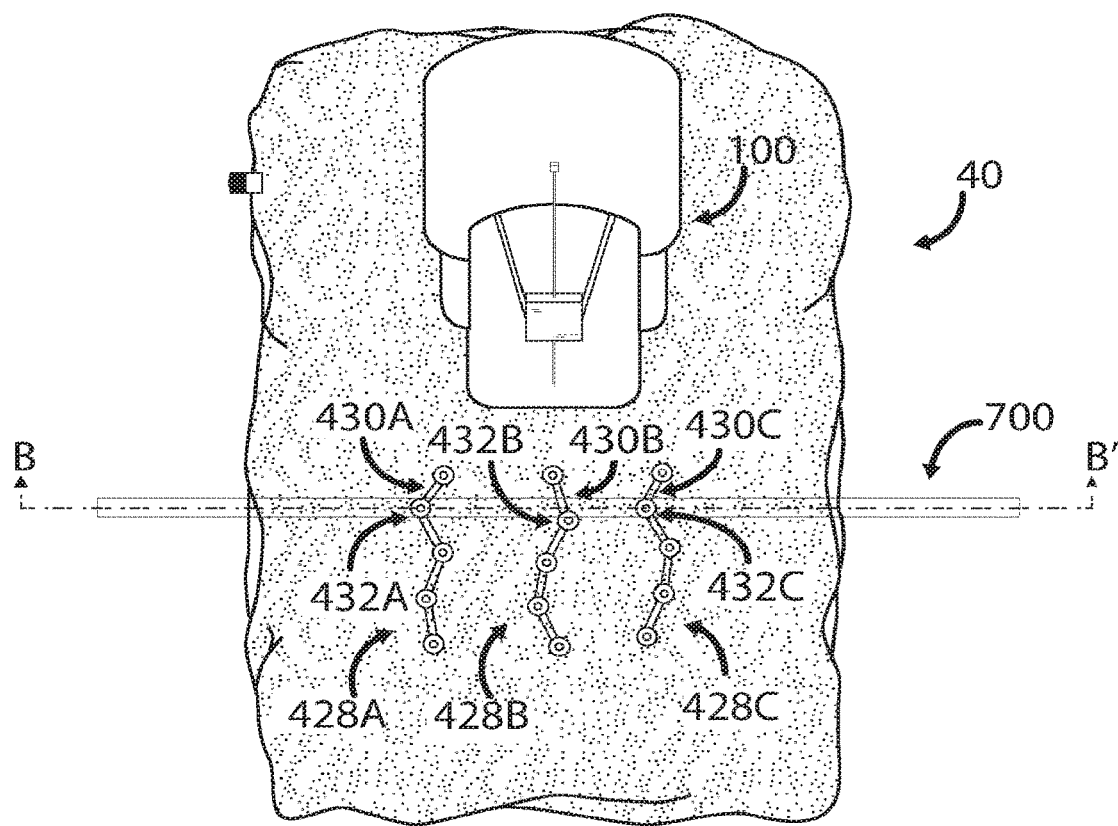
FIG. 7A shows a top view of the exemplary mounting pad, adjustable registration frame and insertion device of FIG. 4B, and an exemplary scanned volume.

FIG. 7A shows a top view of the exemplary mounting pad 40 of FIGS. 4A-4B and an insertion device 100 coupled thereto, after vacuum has been applied to the mounting pad 40. Once vacuum is applied, there is no motion of any rod or rod assembly relative to another rod or rod assembly and of any rod or rod assembly relative to the insertion device 100. The registration frame in the embodiment shown in FIG. 7A is comprised of three articulated rod assemblies 428A, 428B and 428C, each having four rods and five joints. Prior to starting the needle insertion procedure, an initial scan is taken, which includes the entire mounting pad 40, with the registration frame therein, and the insertion device 100 coupled thereto. The spatial angles, MDPs and RPCSs are then calculated and stored, in the same manner as explained in detail above with regard to FIG. 5.

During the insertion procedure, real-time scans are taken, which are limited in volume in order to minimize radiation exposure to the subject and to the medical staff. The number of frames taken during the scan and the spacing between the frames may be determined by the user (e.g., physician), or they may be a system requirement.

The scanned volume 700 may be transverse, as shown in FIG. 7A, or it may be diagonal or have any other orientation relative to the axis of the mounting pad 40. The exemplary scanned volume 700 includes portions of one rod of each of the three articulated rod assemblies 428A, 428B and 428C— rods 430A, 430B and 430C—as well as portions of one joint of each of the three articulated rod assemblies 428A, 428B and 428C—joints 432A, 432B and 432C. It is to be understood, however, that the scanned volume does not necessarily include rods of all the articulated rod assemblies 428A, 428B and 428C of the registration frame. Further, the scanned volume 700 may include more than one rod of the same articulated rod assembly.

Figure 7B:
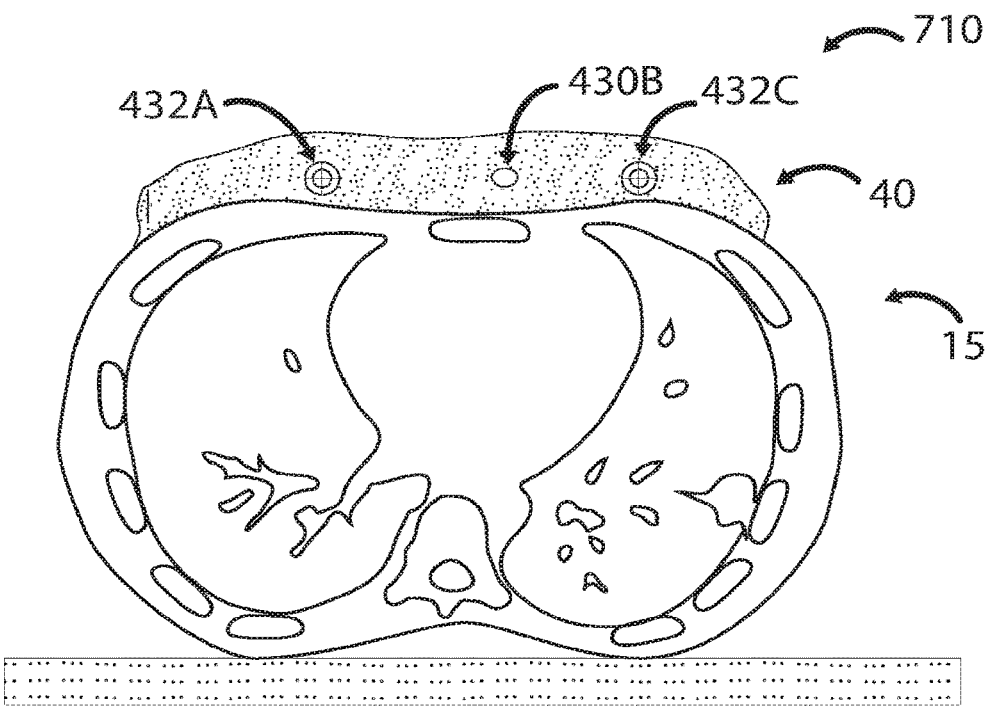
FIG. 7B shows an exemplary image frame of the scanned volume of FIG. 7A.

FIG. 7B shows an exemplary image frame 710 of the scanned volume 700. This exemplary image frame 710 shows a transverse cross-section of the patient's body 15 and of the mounting pad 40 positioned on the patient's body 15, taken along axis BB' in FIG. 7A. Included in the image frame 710 are cross-sections of one rod 430B and two joints 432A and 432C of the registration frame.

Figure 8:
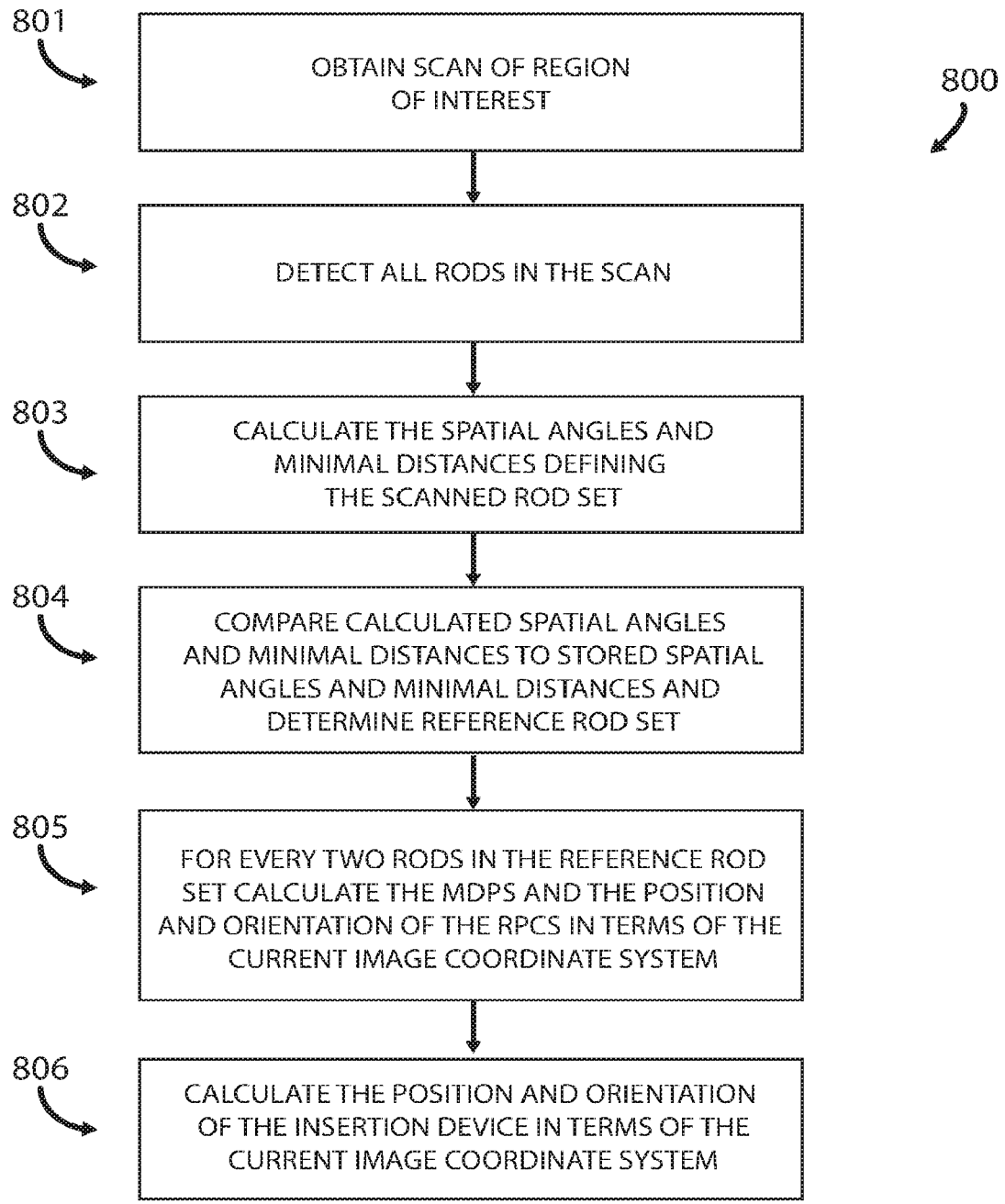
FIG. 8 shows a flowchart of the steps executed in an exemplary method for determining the position and orientation of the insertion device relative to the image space during the tool insertion procedure, using the adjustable registration frame of FIG. 4B.

FIG. 8 shows a flowchart 800 of the steps executed in an exemplary method for determining the position and orientation of the insertion device 100 relative to the image space at any moment during the insertion procedure, using the adjustable registration frame shown in FIGS. 4A-4B.

In step 801, a scan of the region of interest, including a portion of the registration frame, as shown in FIGS. 7A-7B, is obtained. The region of interest to be scanned may be determined such that it encompasses the target (e.g., tumor), and/or the needle tip, for example.

In step 802, all the rods which are included in the scan are detected using image processing techniques. All the rods which are included in a specific scan may be referred to as "rod set".

In step 803, the minimal distances and spatial angles between every two rods which are included in the scan, i.e., every rod pair in the rod set, are calculated. It is to be understood that if the rod set includes more than two rods, it may be sufficient to calculate the minimal distances and spatial angles for only several two rod subsets in order to uniquely define the rod set. For example, if a rod set includes three rods: rod a, rod b and rod c, it may be sufficient to calculate the minimal distances and spatial angles between rod a and rod b and between rod a and rod c, for example, since the minimal distance and spatial angle between rod b and rod c are dictated by the minimal distances and spatial angles between rod a and rod b and between rod a and rod c.

It can be appreciated that in order to determine the minimal distance and the spatial angle between two rods, there is a need for at least two image frames taken within the scanned volume.

In step 804, the calculated minimal distances and spatial angles are compared to the minimal distances and spatial angles which were calculated and stored during the preparation stage of the registration procedure (see step 505 in FIG. 5), and a reference rod set is determined, i.e., it is identified which rods appear in the scan, in their entireties or portions therefrom, and these rods will serve as the reference set for determining the position and orientation of the registration frame relative to the coordinate system of the current image space. Since the minimal distance and spatial angle between the rods do not change as long as vacuum is maintained, the minimal distances and spatial angles can be used to trace the rods and determine which rods appear in the scan.

It can be appreciated that this step may comprise several iterations until the best matching rod set is determined as the reference rod set. Due to noise in the scan, the calculated minimal distances and spatial angles may produce, when compared to the stored minimal distances and spatial angles, several possible reference rod pairs. However, some rod pairs' combinations (i.e., two or more rod pairs together) may be impossible geographically, i.e., they may be located on the registration frame such that it is impossible for them to be included together in the scanned volume. Thus, the reference rod set may be the rod set which is determined, after several iterations, to be the best matching set in terms of both calculated values—minimal distances and spatial angles—and geographic logic.

It can further be appreciated, in light of the above, that in order to achieve effective identification of the reference rod set, the registration frame should preferably be designed such that at least three rods are always included in the scanned volume, regardless of how the scanned volume is selected, and/or the scanned volume should be selected such that at least three rods are included in it.

In step 805, for every two rods in the reference rod set, the MDPs and the position and orientation of the RPCS(s) in terms of the coordinate system of the current image are calculated.

In step 806, the position and orientation of the insertion device in terms of the coordinate system of the current image space is calculated. Since there is no relative movement between the registration frame and the insertion device after vacuum is applied to the mounting pad and as long as the vacuum is not cancelled, the positions and orientations of the RPCSs in terms of the coordinate system of the insertion device, as calculated in the preparation stage of the registration procedure (see FIG. 5), remain unchanged. Thus, the position and orientation of the insertion device in terms of the coordinate system of the current image space can be calculated using the known positions and orientations of the RPCSs which are included in the scanned volume (i.e., the RPCSs of the reference rod set) in terms of the coordinate system of the insertion device, and the positions and orientations of those RPCSs in terms of the coordinate system of the current image space, as calculated in step 805.

Since the position and orientation in terms of the coordinate system of the current image is calculated in step 805 for each RPCS individually, then, in some implementations, in order to calculate the position and orientation of the insertion device in terms of the current image coordinate system, all the positions and orientations of the RPCSs calculated in step 805 are combined together to determine the optimized transformation which yields the smallest overall error (e.g., using the least squares method). In other implementations, the insertion device's position and orientation in terms of the current image coordinate system is calculated based on the position and orientation of each RPCS separately, and the calculated positions and orientations of the insertion device according to each RPCS are then combined to determine the optimized transformation of the insertion device in terms of the current image coordinate system.

Once the position and orientation of the insertion device in terms of the coordinate system of the current image space has been determined, the operator of the insertion system can provide the insertion device with accurate instructions for steering the medical tool (e.g., needle) towards the target.

Reference is now made to FIGS. 9A-12, which illustrate another exemplary implementation of the system and method of the present disclosure. In this implementation, the one or more registration members of the mounting pad are configured as semi-flexible elements, such as strips, and the insertion device's position relative to the current image space is determined based on calculating the positions and orientations of the semi-flexible strips relative to the current image space and the previously calculated (and fixed) position and orientation of the semi-flexible strips relative to the insertion device, as will be explained in detail hereinbelow.

Figure 9A:
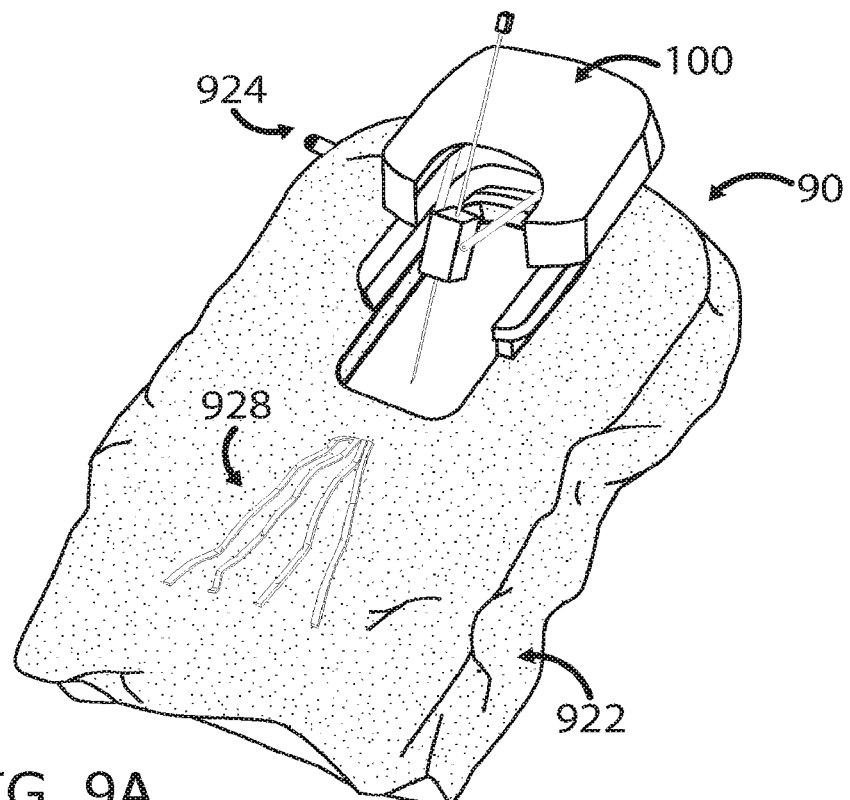
FIG. 9A shows a perspective view of an exemplary mounting pad with another adjustable registration frame, and an insertion device coupled thereto, prior to application of vacuum to the mounting pad.
Figure 9B:
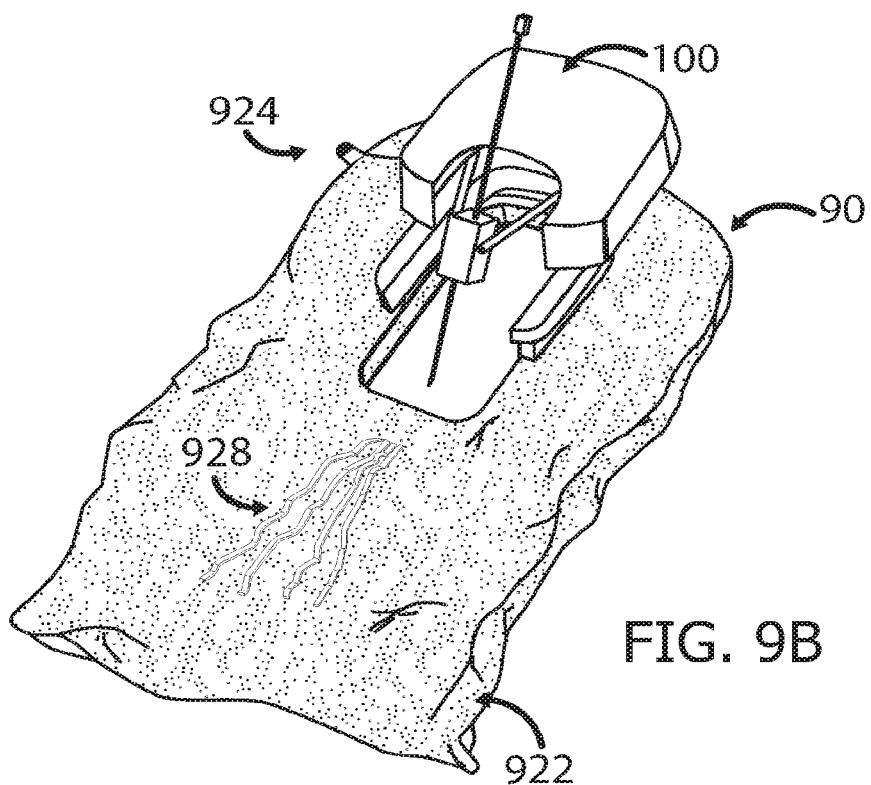
FIG. 9B shows a perspective view of the exemplary mounting pad with the exemplary adjustable registration frame and insertion device of FIG. 9A, after application of vacuum to the mounting pad.

FIG. 9A shows a perspective view of an exemplary mounting pad 90 configured as a flexible sac/cushion filled with granules 922, and an insertion device 100 coupled thereto, prior to application of vacuum on the mounting pad 90. It is to be understood that, although not shown, application of vacuum is carried out only after the mounting pad 90 has been placed on the subject's body and secured thereto, for example, using straps (not shown in FIG. 9A). The insertion device 100 may be coupled to the mounting pad 90 either before or after placement of the mounting pad 90 on the subject's body. In this implementation, the registration frame is comprised of four semi-flexible strips 928. It is to be understood that the use of four strips is merely one example, and the registration frame may include any number of semi-flexible strips, as long as unique identification of the semi-flexible strips included in each scan, which is required for the registration procedure (see below), is enabled. The semi-flexible strips 928 are preferably flexible in one direction and rigid in the direction perpendicular to the first direction, e.g., configured as cable ties/tie-wraps. The adjustable registration frame may comprise a plurality of semi-flexible strips 928 originating from a single vertex, as shown in FIG. 9A. However, it can be appreciated that the semi-flexible strips 928 may otherwise be positioned entirely separate from one another. The strips 928 may be coupled to the mounting pad's cover, either as an integral part of the cover or removably coupled thereto. In such cases, the strips 928 may be coupled either to the cover's external surface (i.e., facing the external environment) or to its internal surface (i.e., facing the granules 922). If the strips 928 are coupled to the mounting pad's cover, then when the pad 90 is in its flexible moldable form, the strips 928 can only move together with its cover. Once vacuum is applied to the mounting pad 90, and it transforms into its solidified/rigid form, as shown in FIG. 9B, the strips 928 can no longer move and they become fixated. Thus, there is also no movement of the strips 928 relative to the insertion device 100. Although not shown in FIG. 9B, it can be appreciated that when vacuum is applied to the mounting pad 90, the bottom portion of the pad 90 may conform, entirely or partially, to the shape of the subject's body.

After the mounting pad has been secured to the subject's body, the insertion device 100 has been coupled to the mounting pad 90, and vacuum has been applied to the mounting pad 90, the clinician can initiate the initial/preparation stage of the registration procedure.

Figure 10:
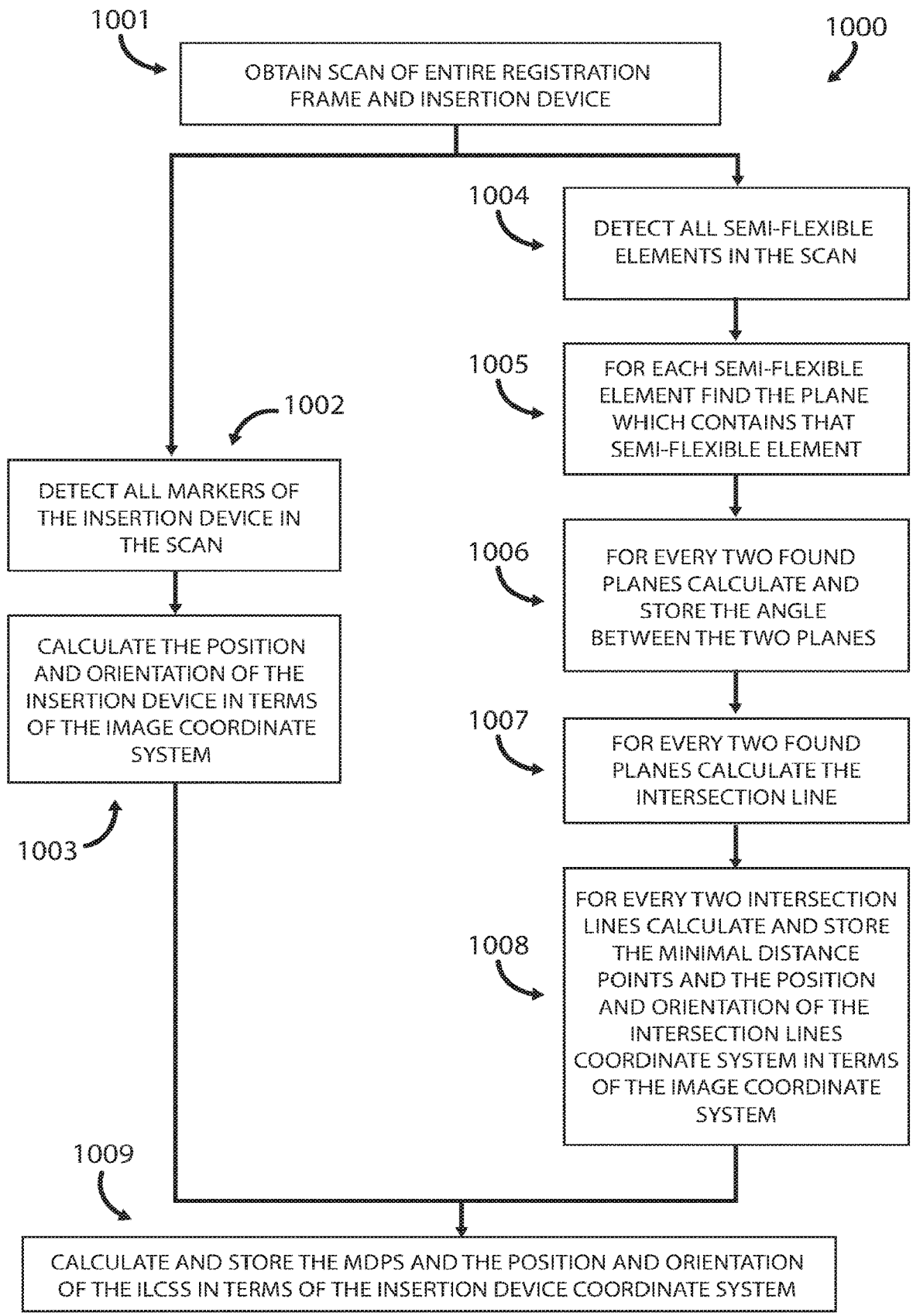
FIG. 10 shows a flowchart of the steps executed in an exemplary initial stage of a registration procedure using the adjustable registration frame of FIG. 9B.

FIG. 10 shows a flowchart 1000 of the steps executed in an exemplary initial/preparation stage of a registration procedure using the semi-flexible strips/elements shown in FIGS. 9A-9B.

In step 1001, an initial scan of the entire registration frame and insertion device is obtained. The number of images taken during the initial scan and the spacing between the images may be determined by the user, or they may be dictated by the system software. The images may be retrieved from the imaging system in any applicable method, such as directly (i.e., an embedded system), using a communication module (e.g., transferring DICOM file(s) over a local area network) or using an external storage unit, such as a CD, DVD, USB portable drive, etc. In some implementations, the scanning may be initiated manually by the user. In other implementations, the scanning may be initiated automatically by the insertion system's software.

In step 1002, all the markers coupled to the insertion device are detected using image processing techniques.

In step 1003, the position and orientation of the insertion device in terms of the coordinate system of the initial image space are calculated.

In step 1004, all the semi-flexible elements (or—strips) are detected in the initial scan using image processing techniques.

In step 1005, for each semi-flexible element, a plane which contains the element, as defined below, is found. Since the semi-flexible elements may have width as opposed to being configured as one dimensional strings, the plane which contains the semi-flexible element may refer, for example, to the plane which contains its longitudinal centerline, i.e., the line connecting the central points of the element's width along the length of the element. Since the semi-flexible elements are flexible only in one direction and are rigid in the direction perpendicular to the first direction (i.e., they cannot bend sideways), only one such plane exists for each semi-flexible element. It can be understood that any plane which is parallel to the plane described above can be found instead, as long as there is consistency in the planes used for all of the elements.

In step 1006, for every two planes found in step 1005, the angle between the two planes is calculated and stored. Since for each semi-flexible element there exists only one plane which contains the longitudinal centerline of that element, the angle between the two planes is unique and can thus be used to trace the semi-flexible elements appearing in subsequent scans.

It can be appreciated that using the angle between the planes in order to identify which semi-flexible elements are included in a particular scan, i.e., by comparing calculated angles to stored angles, as will be described hereinafter, is merely one example of how the semi-flexible elements can be identified. The semi-flexible elements may be identified using any other suitable method, such as adding identifying marks to several or all of the elements (e.g., small protrusions, bristles, etc.), using elements having different characteristics (e.g., width) or materials, calculating and comparing the angle between the different planes' intersection lines (see below), and so forth.

In step 1007, for every two planes found in step 1005, the line where the two planes intersect is found. Since for each semi-flexible element there exists only one plane which contains the longitudinal centerline of that element, the line where such planes of two elements intersect is single and unique.

In step 1008, for every two intersection lines found in step 1007, the minimal distance points ("MDPs") and the position and orientation of the intersection lines' coordinate system (hereinafter also referred to as "ILCS") in terms of the coordinate system of the initial image space are calculated. If two intersection lines intersect each other, then the minimal distance between them is zero and there is a single MDP—the intersection point.

In step 1009, the positions and orientations of the ILCSs in terms of the coordinate system of the insertion device are calculated, based on the position and orientation of the insertion device in terms of the coordinate system of the initial image space, as calculated in step 1003, and the positions and orientations of the ILCSs in terms of the coordinate system of the initial image space, as calculated in step 1008.

Since there is no relative movement between the registration frame and the insertion device after vacuum is applied to the mounting pad, the positions and orientations of the ILCSs in terms of the coordinate system of the insertion device remain unchanged, until the vacuum is cancelled. This enables the insertion device to be positioned outside the scanned volume, as the position and orientation of the insertion device in terms of the coordinate systems of each of the images obtained throughout the insertion procedure can be calculated based on the known positions and orientations of the ILCSs in terms of the coordinate system of the insertion device, and the calculation of the positions and orientations of the ILCSs that are included in the scanned volume in terms of the coordinate system of the specific new image, as described in detail in FIG. 12 hereinbelow.

Figure 11A:
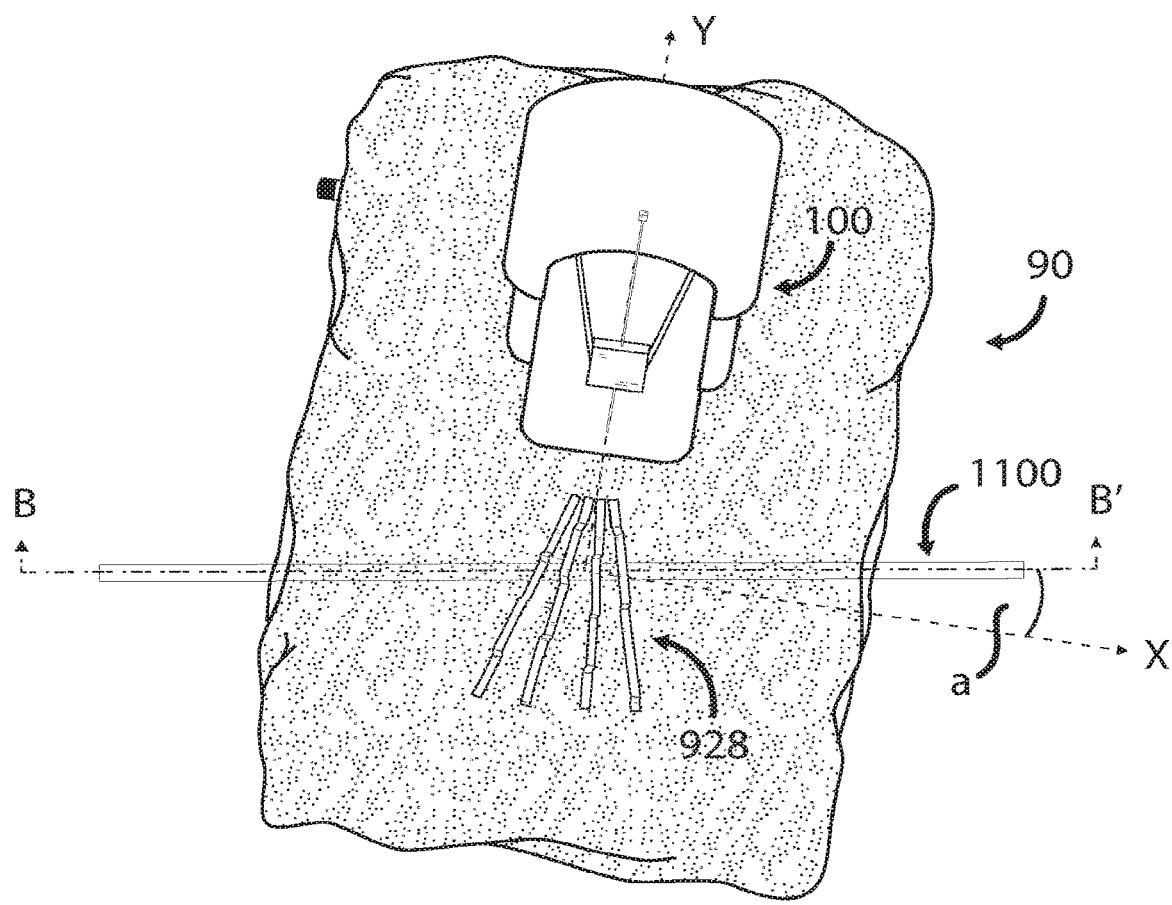
FIG. 11A shows a top view of the exemplary mounting pad, adjustable registration frame and insertion device of FIG. 9B, and an exemplary scanned volume.

FIG. 11A shows a top view of the exemplary mounting pad 90 of FIG. 9B with an insertion device 100 coupled thereto. Since vacuum has been applied to the mounting pad 90, there is no relative motion amongst the different semi-flexible elements/strips 928, between the strips 928 and the surface (i.e., the cover of the mounting pad 90) and between the surface and the insertion device 100. The shown exemplary registration frame is comprised of four strips 928. Prior to starting the needle insertion procedure, a reference scan is taken, which includes the entire mounting pad 90, with the registration frame, and the insertion device 100 coupled thereto. The plane which contains the longitudinal centerline of each semi-flexible strip is then found, and the angle between each two planes is calculated and stored. Then, the lines where each two planes intersect are found, and their MDPs and the transformations of their ILCSs in terms of the coordinate system of the initial image space are calculated and stored. All as explained in detail above with regard to FIG. 10. The real-time scans, taken during the insertion procedure, are then limited in volume, in order to minimize radiation exposure to the subject and the medical staff. Multiple image frames may be taken within the scanned volume. The number of frames taken during the scan and the spacing between the frames may be determined by the user, or they may be a system requirement.

In FIG. 11A the mounting pad 90 is placed diagonally across the subject's body (not shown), and therefore the exemplary scanned volume 1100 is at an angle "a" relative to the X axis of the mounting pad 90. It can be appreciated, that the scanned volume 1100 does not necessarily include portions of each of the semi-flexible strips 928.

Figure 11B:
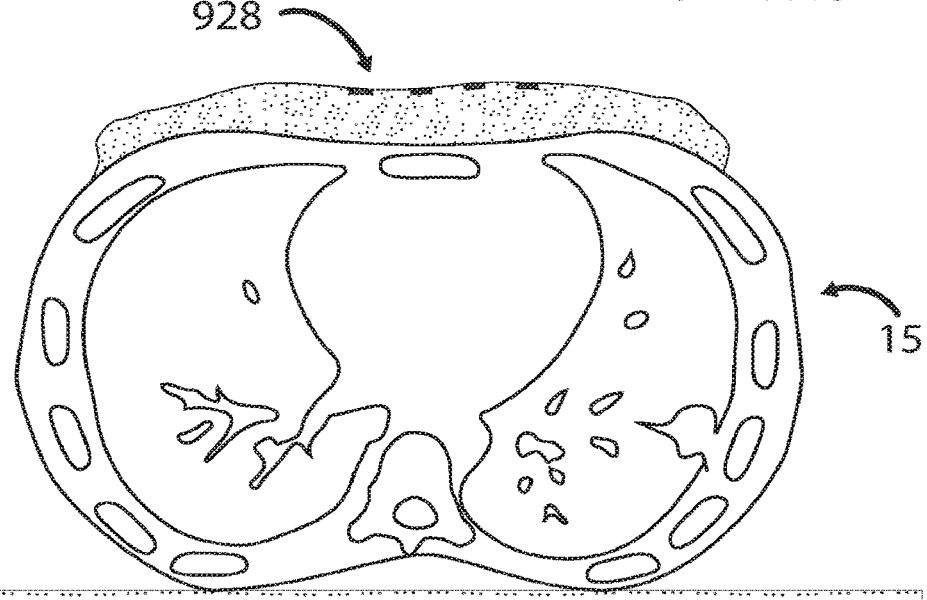
FIG. 11B shows an exemplary image frame of the scanned volume of FIG. 11A.

FIG. 11B shows an exemplary image frame 1110 of the scanned volume 1100. Since the mounting pad 90 is placed diagonally across the subject's body in this case, the exemplary image frame 1110 is a diagonal cross-section of the mounting pad 90, taken along axis BB' in FIG. 11A, and it includes diagonal cross-sections of the four semi-flexible strips 928. As shown, in the implementation depicted in FIGS. 11A-11B, the semi-flexible strips 928 are coupled to the inner surface of the mounting pad's cover.

Figure 12:
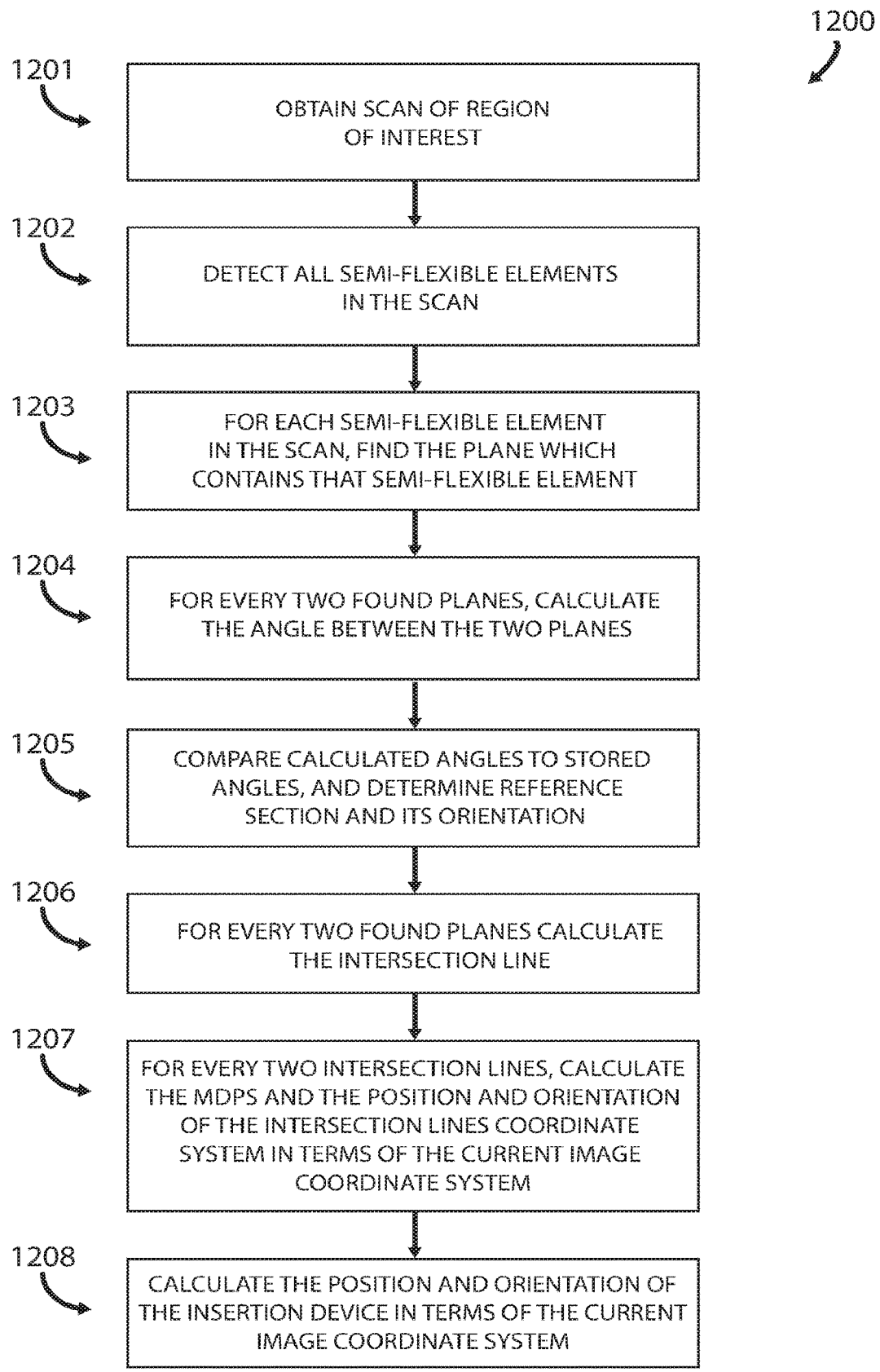
FIG. 12 shows a flowchart of the steps executed in an exemplary method for determining the position of the insertion device relative to the image space during the tool insertion procedure, using the adjustable registration frame of FIG. 9B.

FIG. 12 shows a flowchart 1200 of the steps executed in an exemplary method for determining the position and orientation of the insertion device 100 relative to the image space at any moment during the needle insertion procedure, using the semi-flexible elements/strips shown in FIGS. 9A-9B.

In step 1201, a scan of the region of interest, including a portion of the registration frame, as shown in FIGS. 11A-11B, is obtained. The region of interest may be determined such that it encompasses the target (e.g., tumor), and/or the needle tip, for example.

In step 1202, all the semi-flexible elements (or—strips), or portions therefrom, which are included in the scan are detected using image processing techniques.

In step 1203, for each semi-flexible element in the scan, the plane which contains that semi-flexible element, or any other plane parallel to that plane, is found. As previously stated with regard to step 1005 in FIG. 10, the plane which contains the semi-flexible element may refer, for example, to the plane which contains its longitudinal centerline.

In step 1204, for every two planes found in step 1203, the angle between the two planes is calculated. As previously stated, since for each semi-flexible element there exists only one plane which contains the longitudinal centerline of that element, for example, the angle between those two planes is unique and can thus be used to trace the semi-flexible elements appearing in the scan. It can be appreciated that in order to find the described unique planes, there is a need for at least two image frames taken within the scanned volume.

In step 1205, the calculated angles are compared to the angles which were calculated and stored during the preparation stage of the registration procedure (see step 1006 in FIG. 10). The reference section and its orientation are then determined, based on the highest correlation found between calculated and stored angles, and it can then be determined which semi-flexible elements are included in the scan.

It can be appreciated that using the angle between the planes in order to identify which semi-flexible elements are included in a particular scan is merely one example of how the semi-flexible elements can be identified. The semi-flexible elements may be identified using any other suitable method, such as identifying marks on several or all of the elements (e.g., small protrusions, bristles, etc.), using elements having different characteristics (e.g., width) or materials, and so forth.

Once it has been determined which semi-flexible elements appear in the scan, the position and orientation of those elements relative to the current image space is calculated, as follows:

In step 1206, for every two planes found in step 1203, the line where the two planes intersect is found. Since for each semi-flexible element there exists only one plane which contains the longitudinal centerline of that element, there also exists only one line where two such planes intersect.

In step 1207, for every two intersection lines found in step 1206, the minimal distance points ("MDPs") and the position and orientation of the intersection lines' coordinate System ("ILCS") in terms of the coordinate system of the current image space is calculated.

In step 1208, the position and orientation of the insertion device in terms of the coordinate system of the current image space is calculated. Since there is no relative movement between the registration frame and the insertion device after vacuum is applied to the mounting pad, and as long as the vacuum is not cancelled, the positions and orientations of the ILCSs in terms of the coordinate system of the insertion device, as calculated in the preparation stage of the registration procedure (see FIG. 10), remain unchanged. Thus, the position and orientation of the insertion device in terms of the coordinate system of the current image space can be calculated using the known positions and orientations of the ILCS s relating to the semi-flexible elements included, at least in part, in the reference section in terms of the coordinate system of the insertion device, and the calculated positions and orientations of those ILCSs in terms of the coordinate system of the current image space (see step 1207).

The transformation of the insertion device in terms of the current image coordinate system is calculated in step 1207 for each ILCS individually, in case there is more than one ILCS, i.e., if there are more than three semi-flexible elements within the scanned volume. Therefore, in some implementations, in order to calculate the transformation of the insertion device in terms of the current image coordinate system, all the transformations of the ILCS s calculated in step 1207 are combined together to determine one optimized transformation which yields the smallest overall error (e.g., using the least squares method). In other implementations, the insertion device's transformation in terms of the current image CS is calculated based on the transformation of each ILCS separately, and the calculated transformations of the insertion device are then combined to determine the optimized transformation of the insertion device in terms of the current image CS.

Once the position and orientation of the insertion device in terms of the coordinate system of the current image space has been determined, the operator of the insertion system can provide the insertion device with accurate instructions for steering the medical tool toward the target.

In an alternative implementation, the registration frame may include, in addition to the semi-flexible strips, one or more threads which cross the semi-flexible strips substantially horizontally. The threads may be stretched across the semi-flexible strips in straight lines or as arches, i.e., forming together with the semi-flexible strips a cobweb-like pattern, for example. The threads should be made up from a material that is visible by the imaging system (e.g., CT, MRI), such as silk.

In this implementation, the points of intersection between the threads and the semi-flexible strips may be detected in the initial scan carried out after vacuum is applied to the mounting pad. The initial scan includes both the insertion device and the entire registration frame, similarly to the above-described implementations. A plurality of coordinate systems, each having its origin at an intersection point (thus also referred to as "intersection point coordinate system" or "IPCS"), may then be calculated relative to the initial image space. In some implementations, The X'Y'Z' vectors of the IPCS may be defined by the semi-flexible strip, the vector perpendicular to the plane formed by the semi-flexible strip and the thread at least at the immediate surrounding of the intersection point, and the cross product of the first two vectors.

The transformation of the insertion device relative to the initial image space is also calculated, and based on these two calculations, the transformation of the IPCSs in terms of the insertion device coordinate system, is calculated. Since after vacuum is applied to the mounting pad there is no relative movement between the registration frame and the insertion device, the transformation of the IPCSs in terms of the insertion device coordinate system remains unchanged until the vacuum is cancelled.

The transformation of the insertion device in terms of the image space in consecutive real-time scans taken during the medical procedure may then be calculated based on the fixed transformation of the IPCSs in terms of the insertion device coordinate system and the newly calculated transformations of the IPCSs in terms of the new image.

It should be noted that after the intersection points are detected in a real-time scan, and before the IPCSs are calculated, there may be a need for an additional step of image processing (e.g., surface matching), in order to correctly identify the mounting pad section appearing in the scan, and its orientation, and thus correctly determine which intersection points are the intersection points detected in the scan. The additional image processing step may be carried out on the entire mounting pad section included in the scan, or it may be carried out on the immediate surrounding of each intersection point separately. Further, the additional image processing step may be carried out first on the entire mounting pad section included in the scan, and then on the immediate surrounding of each intersection point, for fine tuning purposes. This additional image processing step may be done, for example, using visual/image descriptors, such as distinct edges or corners in the semi-flexible strips, distinct patterns in the surface of the mounting pad or distinct patterns in the granules located in the scanned volume.

Although particular implementations have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the disclosure as defined by the claims. For example, the logic flows depicted in the accompanying figures and described herein do not necessarily require the particular order shown, or sequential order, to achieve desirable results. Other aspects, advantages, and modifications are considered to be within the scope of the following claims. The claims presented are representative of the implementations and features disclosed herein. Other unclaimed implementations and features are also contemplated. Accordingly, other implementations are within the scope of the following claims.

The invention claimed is:

1. A method for determining the real-time position and orientation of an automated medical device relative to an image space during an image-guided procedure, using a mounting apparatus configured for mounting on a body of a subject and for coupling the automated medical device thereto, at least one registration member positioned either on or inside the mounting apparatus, and a processor, the method comprising:
    obtaining one or more initial images of the mounting apparatus and the automated medical device coupled thereto;
    detecting the at least one registration member in the one or more initial images;
    calculating the position and orientation of the at least one registration member relative to the image space in the one or more initial images;
    calculating the position and orientation of the automated medical device relative to the image space in the one or more initial images;
    determining the position and orientation of the at least one registration member relative to the automated medical device based on the calculated positions and orientations of the automated medical device and of the at least one registration member relative to the image space in the one or more initial images;
    obtaining one or more real-time images of a region of interest, the one or more real-time images including at least two portions of the at least one registration member;
    detecting the at least two portions of the at least one registration member in the one or more real-time images;
    determining the real-time position and orientation of the at least two portions of the at least one registration member relative to the image space in the one or more real-time images; and
    determining the real-time position and orientation of the automated medical device relative to the image space in the one or more real-time images based on the real-time position and orientation of the at least two portions of the at least one registration member relative to the image space and the position and orientation of the at least one registration member relative to the automated medical device determined based on the one or more initial images.

2. The method of claim 1, comprising, upon detecting the at least one registration member in the one or more initial images, calculating initial values of one or more predetermined geometric parameters for the at least one registration member.

3. The method of claim 2, comprising, upon detecting the at least two portions of the at least one registration member in the one or more real-time images, calculating real-time values of the one or more predetermined geometric parameters for the at least two portions of the at least one registration member.

4. The method of claim 3, comprising comparing the real-time values of the one or more predetermined geometric parameters to the initial values of the one or more predetermined geometric parameters and identifying the at least two portions of the at least one registration member.

5. The method of claim 2, wherein the predetermined geometric parameters comprise one or more of: angle, distance, length, shape, plane, relative position and coordinate system.

6. The method of claim 1, comprising detecting in the one or more initial images, one or more registration markers attached to the automated medical device.

7. The method of claim 1, wherein the at least one registration member comprises one or more rods.

8. A method for determining the real-time position and orientation of an automated medical device relative to an image space during an image-guided procedure, the method comprising:
providing a system comprising:
a mounting apparatus configured for mounting on a body of a subject and for coupling the automated medical device thereto;
at least one registration member positioned either on or inside the mounting apparatus, such that during the image-guided procedure, there is substantially no relative movement between the at least one registration member and the automated medical device coupled to the mounting apparatus; and
at least one processor;
obtaining one or more real-time images of a region of interest in the body of the subject, the one or more real-time images including at least two portions of the at least one registration member;
detecting the at least two portions of the at least one registration member in the one or more obtained real-time images;
determining the real-time position and orientation of the at least two portions of the at least one registration member relative to the image space; and
determining the real-time position and orientation of the automated medical device relative to the image space based on the determined real-time position and orientation of the at least two portions of the at least one registration member relative to the image space and a predetermined relationship between the automated medical device and the at least one registration member.

9. The method of claim 8, wherein the at least one registration member comprises one or more rods.

10. The method of claim 9, wherein the step of determining the real-time position and orientation of the at least two portions of the at least one registration member relative to the image space comprises calculating a spatial angle between at least two rods of the one or more rods.

11. The method of claim 9, wherein the step of determining the real-time position and orientation of the at least two portions of the at least one registration member relative to the image space comprises:
calculating the minimal distance between the at least two rods, the minimal distance points on the at least two rods and a rod coordinate system of the at least two rods; and
calculating the real-time position and orientation of the rod coordinate system relative to the image space.

12. The method of claim 8, further comprising determining the predetermined relationship between the automated medical device and the at least one registration member using one or more initial images.

13. A system for determining the real-time position and orientation of an automated medical device relative to an image space during image-guided procedures, the system comprising:
a mounting apparatus configured for mounting on a body of a subject and for coupling the automated medical device thereto;
at least one registration member positioned either on or inside the mounting apparatus; and
a processor configured to:
detect at least a portion of the at least one registration member in one or more real-time images obtained from an imaging system;
determine the real-time position and orientation of the at least a portion of the at least one registration member relative to the image space; and
determine the real-time position and orientation of the automated medical device relative to the image space based on the determined real-time position and orientation of the at least a portion of the at least one registration member relative to the image space and a predetermined relationship between the automated medical device and the at least one registration member.

14. The system of claim 13, wherein the processor is configured to determine the predetermined relationship between the automated medical device and the at least one registration member using one or more initial images obtained from the imaging system.

15. The system of claim 13, wherein the at least one registration member comprises one or more rods.

16. The system of claim 13, wherein the at least one registration member comprises one or more semi-flexible elements.

17. The system of claim 13, further comprising one or more registration markers attached to the automated medical device, and wherein the processor is configured to detect the one or more registration markers in one or more images obtained from the imaging system.

* * * * *